(12) United States Patent
Kikuchi

(10) Patent No.: US 11,571,111 B2
(45) Date of Patent: Feb. 7, 2023

(54) ENDOSCOPE SCOPE, ENDOSCOPE PROCESSOR, AND ENDOSCOPE ADAPTOR

(71) Applicant: OLYMPUS CORPORATION, Hachioji (JP)

(72) Inventor: Sunao Kikuchi, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 973 days.

(21) Appl. No.: 16/380,630

(22) Filed: Apr. 10, 2019

(65) Prior Publication Data

US 2019/0231178 A1  Aug. 1, 2019

Related U.S. Application Data

(63) Continuation of application No. PCT/JP2016/081289, filed on Oct. 21, 2016.

(51) Int. Cl.
*A61B 1/00* (2006.01)
*A61B 1/06* (2006.01)
*A61B 1/04* (2006.01)

(52) U.S. Cl.
CPC .... *A61B 1/000095* (2022.02); *A61B 1/00186* (2013.01); *A61B 1/04* (2013.01);
(Continued)

(58) Field of Classification Search
None
See application file for complete search history.

(56) References Cited

U.S. PATENT DOCUMENTS

2006/0082666 A1  4/2006  Abe et al.
2007/0126897 A1  6/2007  Nagakura
(Continued)

FOREIGN PATENT DOCUMENTS

EP  1650981 A2  4/2006
EP  2194721 A2  6/2010
(Continued)

OTHER PUBLICATIONS

International Search Report (ISR) dated Dec. 20, 2016 issued in International Application No. PCT/JP2016/081289.
(Continued)

*Primary Examiner* — Rebecca A Volentine
(74) *Attorney, Agent, or Firm* — Holtz, Holtz & Volek PC

(57) ABSTRACT

An endoscope scope includes: an imaging device that acquires image information; a color filter disposed on pixels of the imaging device and in which primary-color pixels and complementary-color pixels coexist; a detector that detects whether or not an image processor that generates an observation image based on the acquired image information via the color filter is compatible with the image information consisting of an array in which the primary-color pixels and the complementary-color pixels coexist; and a converter that performs Bayer-conversion processing for converting the image information to a Bayer array in a case in which the detector detects that the image processor is not compatible with the image information consisting of the array, and that does not perform the Bayer-conversion processing on the image information in a case in which the detector detects that the image processor is compatible with the image information consisting of the array.

17 Claims, 18 Drawing Sheets

(52) U.S. Cl.
CPC ........ *A61B 1/0661* (2013.01); *A61B 1/00045* (2013.01); *A61B 1/0638* (2013.01)

(56) References Cited

U.S. PATENT DOCUMENTS

| | | |
|---|---|---|
| 2010/0141812 A1 | 6/2010 | Hirota |
| 2011/0071352 A1 | 3/2011 | Ozawa et al. |
| 2013/0153748 A1* | 6/2013 | Suzuki ............... H04N 9/04555 250/208.1 |
| 2013/0286260 A1 | 10/2013 | Hirota |
| 2015/0109496 A1 | 4/2015 | Hirota |
| 2015/0241611 A1 | 8/2015 | Hirota |
| 2015/0264325 A1 | 9/2015 | Hirota |
| 2016/0270643 A1 | 9/2016 | Sasaki |
| 2016/0373709 A1 | 12/2016 | Hirota |
| 2017/0164817 A1 | 6/2017 | Shiraishi et al. |
| 2018/0007338 A1 | 1/2018 | Hirota |
| 2018/0041719 A1* | 2/2018 | Kurata ................... H04N 9/083 |

FOREIGN PATENT DOCUMENTS

| | | |
|---|---|---|
| EP | 2301415 A1 | 3/2011 |
| EP | 3085300 A1 | 10/2016 |
| EP | 3173011 A1 | 5/2017 |
| JP | 2006115963 A | 5/2006 |
| JP | 2007184905 A | 7/2007 |
| JP | 4683121 B2 | 5/2011 |
| JP | 2012005807 A | 1/2012 |
| JP | 2014103597 A | 6/2014 |
| JP | 2014233387 A | 12/2014 |
| JP | 2015116328 A | 6/2015 |
| JP | 2015217084 A | 12/2015 |
| WO | 2016121464 A1 | 8/2016 |

OTHER PUBLICATIONS

Written Opinion dated Dec. 20, 2016 issued in International Application No. PCT/JP2016/081289.

* cited by examiner

FIG. 14
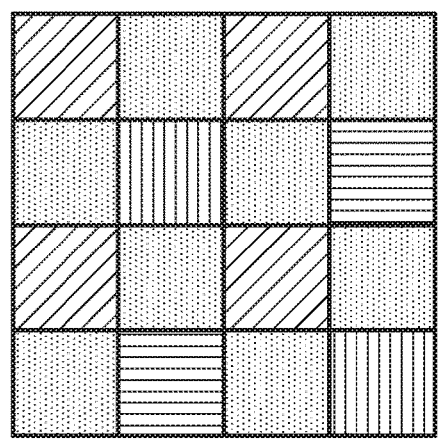
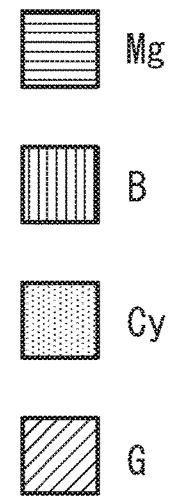
FIG. 15
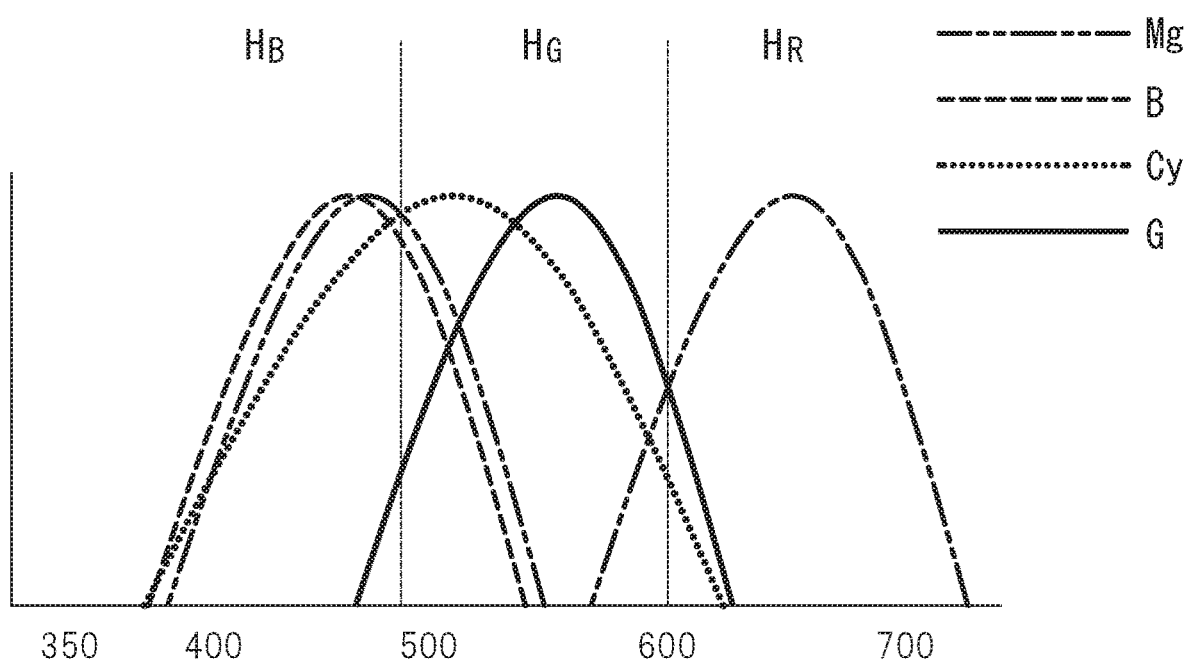

ENDOSCOPE SCOPE, ENDOSCOPE PROCESSOR, AND ENDOSCOPE ADAPTOR

CROSS-REFERENCE TO RELATED APPLICATIONS

This is a continuation of International Application PCT/JP2016/081289, with an international filing date of Oct. 21, 2016, which is hereby incorporated by reference herein in its entirety.

TECHNICAL FIELD

The present invention relates to an endoscope scope, an endoscope processor, and an endoscope adaptor.

BACKGROUND ART

In the related art, endoscope apparatuses are widely employed in various types of examination in the medical field and the industrial field. By inserting, into a body cavity of a subject such as a patient, a flexible inserted portion that has a long, thin shape and that is provided with, at a distal end thereof, an imaging device having a plurality of pixels, it is possible to acquire a body-interior image without making an incision in the patient; therefore, the burden on the subject is low, and thus, the use of medical endoscope apparatuses is becoming more common.

As observation systems of such endoscope apparatuses, a white-light observation (WLI: White Light Imaging) system employing white illumination light (white illumination light) and a narrow-band light observation (NBI: Narrow Band Imaging) system employing illumination light (narrow-band illumination light) consisting of two narrow band lights that are in a blue-light wavelength band and a green-light wavelength band, respectively, are widely known. With the narrow-band light observation system, it is possible to obtain an image in which capillaries, fine mucosal patterns, etc. that are present in a mucosal surface layer (living-organism surface layer) of a living organism are displayed by being emphasized, and it is possible to more accurately find a lesion in the mucosal surface layer of the living organism. Regarding the observation method for such an endoscope apparatus, there is a demand for performing observation by switching between the white-light observation system and an observation system based on special light such as the narrow-band light.

In an endoscope apparatus that generates a color image by means of the above-described observation system and displays said image, in order to acquire an image by means of a single-plate imaging device, color filters are provided on a light-receiving surface of the imaging device, light in the wavelength band that is allowed to pass through the color filters is received by the individual pixels of the imaging device, and electrical signals for color components in accordance with the light of that wavelength band are generated. Then, interpolation processing referred to as demosaicing processing, in which signal values are calculated for color components that are missing as a result of the light not passing through the color filters at the individual pixels, is performed, thus generating a color image. The color filters provided on the imaging device are separately arrayed on the pixels, in general, by assuming that filters that individually allow light in red (R), green (G), and blue (B) wavelength bands to pass therethrough serve as one filter unit (array). This filter array is referred to as a primary-color Bayer array.

In recent years, in order to achieve a sense of high resolution both with the white-light observation system and the narrow-band light observation system in a living organism, a filter arrangement in which not only the primary-color color filters but also color filters for complementary colors, such as cyan (Cy) and magenta (Mg), coexist has been disclosed (for example, see Patent Literature 1). By mixing these complementary-color pixels and the primary-color pixels, it is possible to obtain a greater amount of information about the blue wavelength band as compared with the case in which only the primary-color pixels are contained, and it becomes possible to achieve a resolution enhancement effect for capillaries or the like in the case of narrow-band light observation.

However, in general, an image-processing apparatus for generating an output image is compatible only with the primary-color Bayer array, and it is necessary to develop a special image-processing apparatus in the case in which an imaging device having a different filter arrangement is employed. Furthermore, in the case in which an endoscope (scope) having an imaging device and an image-processing apparatus are separate pieces, as in an endoscope apparatus, it is necessary to consider various combinations of the endoscope (scope) and the image-processing apparatus. Accordingly, there is a problem in that a correct output result is not obtained in the case in which an endoscope (scope) having an imaging-acquisition device that has the filter arrangement described in Patent Literature 1 is connected to an image-processing apparatus for the primary-color Bayer array.

In response to such a problem, a technique for converting image-acquisition data of an RGBW filter arrangement, in which primary-color pixels and white (W) pixels coexist, to the primary-color Bayer array has been disclosed (for example, see Patent Literature 2).

CITATION LIST

Patent Literature

{PTL 1} Japanese Unexamined Patent Application, Publication No. 2015-116328
{PTL 2} Publication of Japanese Patent No. 4683121

SUMMARY OF INVENTION

A first aspect of the present invention is an endoscope scope including: an imaging device that acquires image information about an imaging subject; a color filter that is disposed on pixels of the imaging device and in which primary-color pixels and complementary-color pixels coexist; a compatibility-detecting portion that detects whether or not an image-processing apparatus that generates an observation image on the basis of the image information acquired by the imaging device via the color filter is compatible with the image information consisting of an array in which the primary-color pixels and the complementary-color pixels coexist; and a conversion processing portion that performs Bayer-conversion processing for converting the image information to be transmitted to the image-processing apparatus from the imaging device to a Bayer array in the case in which the compatibility-detecting portion detects that the image-processing apparatus is not compatible with the image information consisting of the array in which the primary-color pixels and the complementary-color pixels coexist, and that does not perform the Bayer-conversion processing on the image information to be transmitted to the image-processing apparatus from the imaging device in the case in which the compatibility-detecting portion detects that the image-processing apparatus is compatible with the image information consisting of the array in which the primary-color pixels and the complementary-color pixels coexist.

A second aspect of the present invention is an endoscope processor including: an Bayer-processing image-processing portion that generates an observation image on the basis of image information acquired by an imaging device of an endoscope scope; an array-detecting portion that detects whether or not the image information output from the imaging device of the connected endoscope scope consists of a Bayer array; and a conversion processing portion that applies Bayer-conversion processing for converting the image information transmitted to the image-processing portion from the imaging device to the Bayer array in the case in which the array-detecting portion does not detect that the image information consists of the Bayer array, and that does not apply the Bayer-conversion processing to the image information transmitted to the image-processing portion from the imaging device in the case in which the array-detecting portion detects that the image information consists of the Bayer array.

A third aspect of the present invention is an endoscope adaptor that connects an endoscope scope that is provided with an imaging device, which acquires image information about an imaging subject, and that is inserted into a body cavity and a Bayer-processing image-processing apparatus, which generates an observation image based on the image information acquired by the imaging device, the endoscope adaptor including: an array-detecting portion that detects whether or not the image information output from the imaging device of the endoscope scope to be connected to the image-processing apparatus consists of the Bayer array; and a conversion processing portion that applies Bayer-conversion processing for converting the image information transmitted to the image-processing apparatus from the imaging device to the Bayer array in the case in which the array-detecting portion does not detect that the image information consists of the Bayer array, and that does not apply the Bayer-conversion processing to the image information transmitted to the image-processing apparatus from the imaging device in the case in which the array-detecting portion detects that the image information consists of the Bayer array.

BRIEF DESCRIPTION OF DRAWINGS

FIG. 14 is a diagram showing an example of the color filter, which is a first modification of the individual embodiments of the present invention.

FIG. 15 is a diagram showing an example of spectral characteristics of the imaging device, which is a first modification of the individual embodiments of the present invention.

DESCRIPTION OF EMBODIMENTS

First Embodiment

An endoscope scope according to a first embodiment of the present invention will be described below with reference to the drawings.

Figure 1:
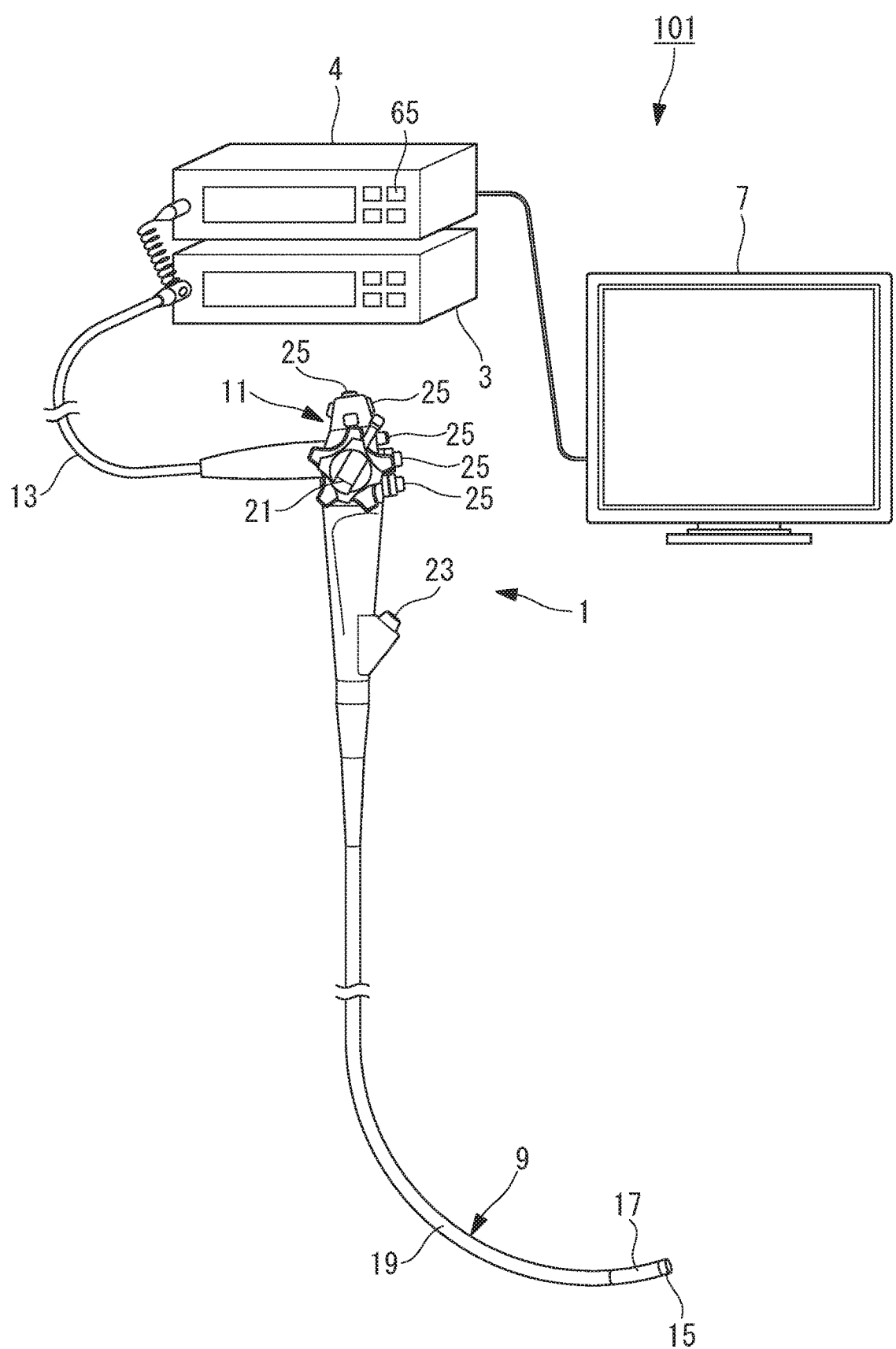
FIG. 1 is a diagram showing, in outline, the configuration of an endoscope apparatus provided with an endoscope according to a first embodiment of the present invention.

An endoscope (endoscope scope) 1 according to this embodiment is employed, for example, in an endoscope apparatus 101, as shown in FIG. 1

Figure 2:
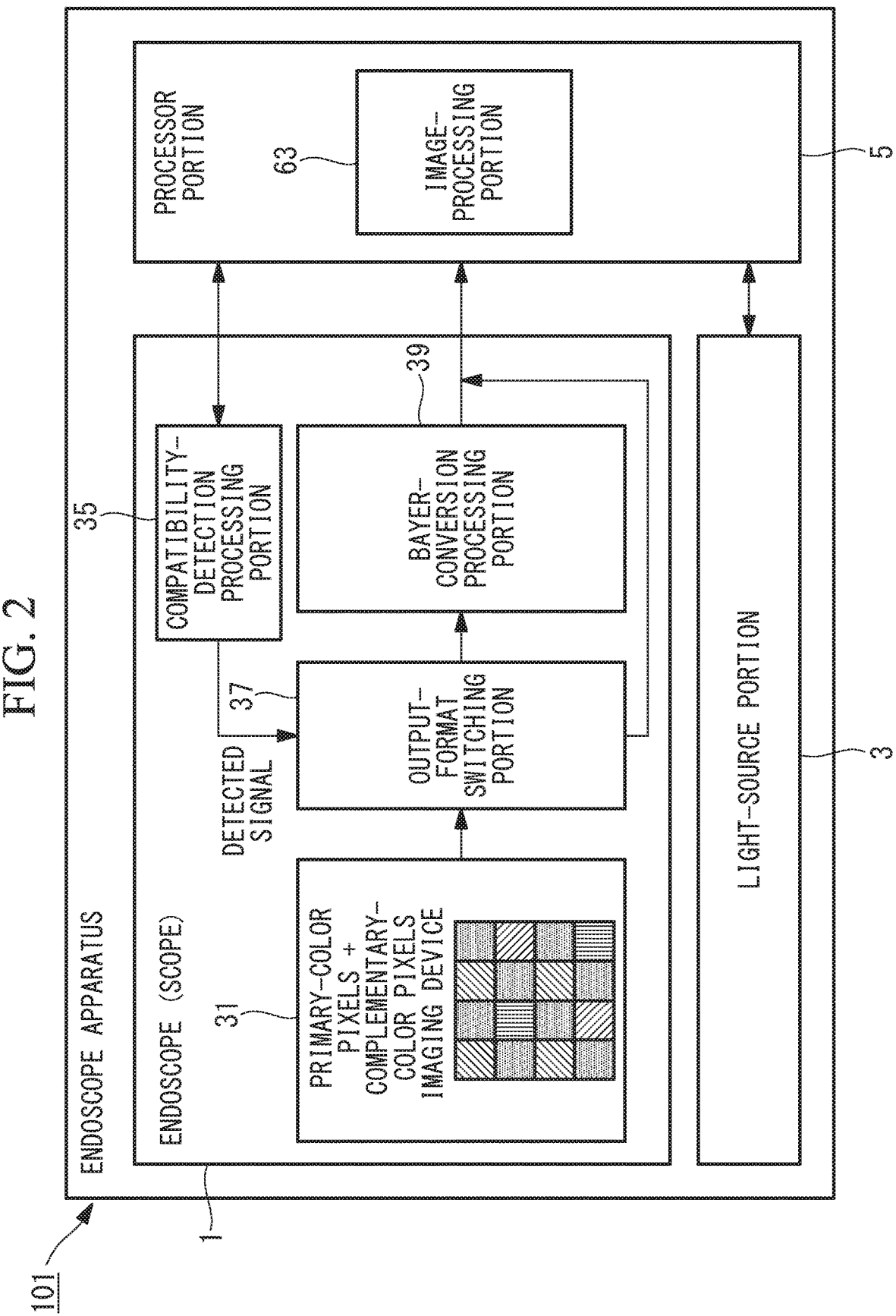
FIG. 2 is a block diagram showing the configuration of the endoscope apparatus in FIG. 1.
Figure 3:
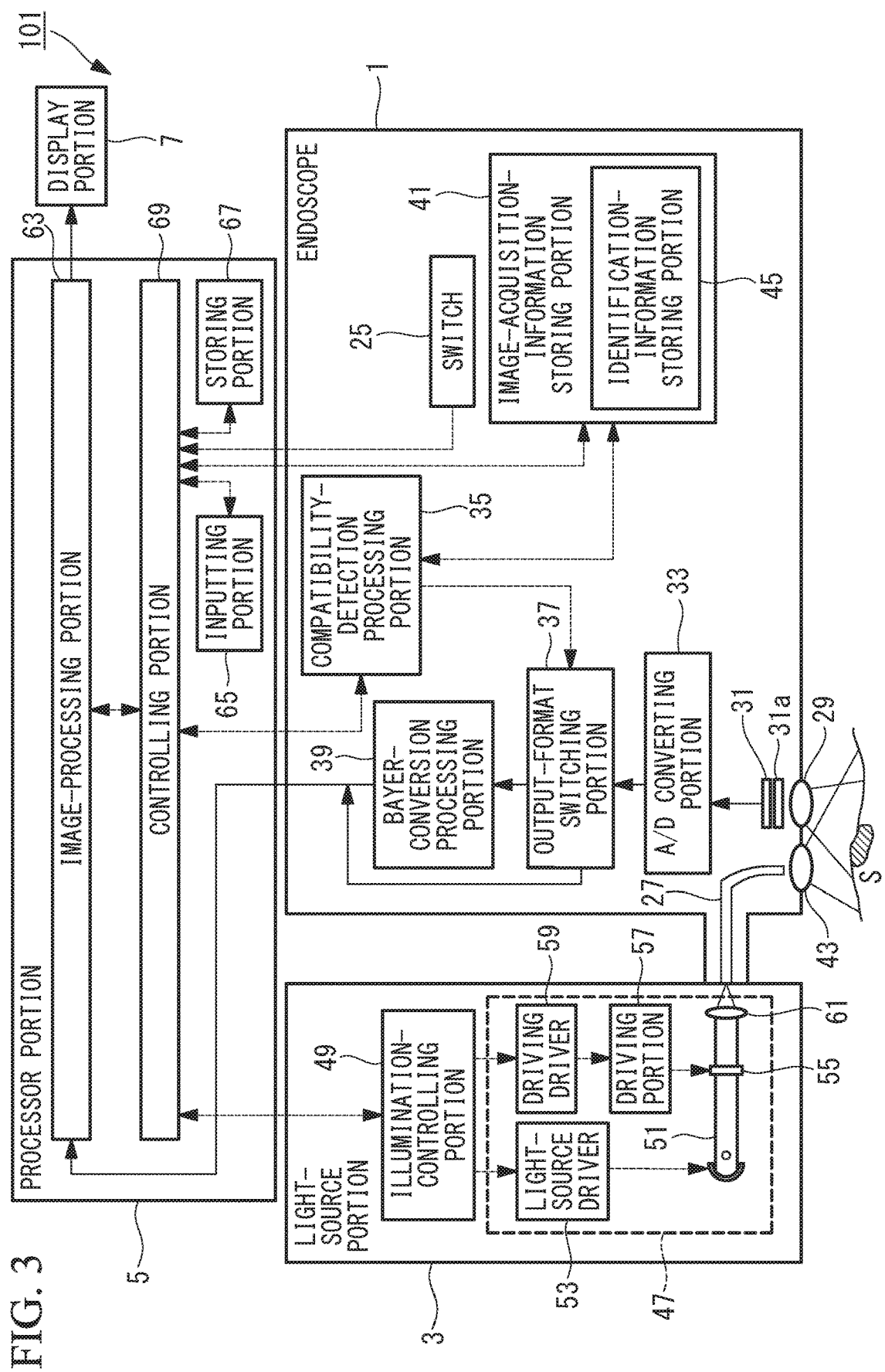
FIG. 3 is a block diagram showing, in detail, the configuration of the endoscope apparatus in FIG. 1.

As shown in FIGS. 1, 2, and 3, the endoscope apparatus 101 is provided with: the endoscope 1 that has an inserted portion 9 to be inserted into a body cavity of a subject (not shown) and that generates image signals (electrical signals, image information) by acquiring a body-interior image at an observation site by means of the inserted portion 9; a light-source portion 3 that generates illumination light to be emitted from a distal end of the inserted portion 9 of the endoscope 1; a processor portion (endoscope processor) 5 that has an image-processing portion 63 that applies predetermined image processing to the image signals acquired by the endoscope 1 and that integrally controls the operation of the entirety of the endoscope apparatus 101; and a display portion 7 that displays the body-interior image to which the image processing has been applied by the processor portion 5.

The endoscope 1 is provided with: the inserted portion 9 that possesses flexibility and that has a long, thin shape; a manipulation portion 11 that is connected on a base-end side of the inserted portion 9 and receives inputs of various types of manipulation signals; and a universal cord 13 that extends in a direction that is different from the direction in which the inserted portion 9 extends from the manipulation portion 11 and that has various types of built-in cables that are connected to the light-source portion 3 and the processor portion 5.

The inserted portion 9 is provided with: a distal-end portion 15 that has a built-in imaging device 31 in which pixels (photodiodes) that receive light are arrayed in a lattice (matrix)-like manner and that generates image signals by performing photoelectric conversion of the light received by the pixels; a bendable bending portion 17 that is freely bendable and formed of a plurality of bending pieces; and an elongated flexible tubular portion 19 that is connected on a base-end side of the bending portion 17 and that possesses flexibility.

The manipulation portion 11 is provided with: a bending knob 21 that causes the bending portion 17 to be bent in top-to-bottom directions and left-to-right directions; a treatment-tool inserting portion 23 with which a treatment tool, such as biological forceps, an electric knife, an examination probe, or the like, is inserted into the body cavity of the subject; and a plurality of switches 25 with which instruction signals for causing the light-source portion 3 to perform the operation for changing the type of the illumination light, manipulation instruction signals for external devices connected to the treatment tool and the processor portion 5, water-feeding instruction signals for feeding water, and suction instruction signals for performing suction are input.

The treatment tool inserted into the treatment-tool inserting portion 23 comes out from an opening (not shown) via a treatment tool channel (not shown) provided at a distal end of the distal-end portion 15.

The universal cord 13 has, built therein, at least a light guide 27 shown in FIG. 3 and a cable assembly (not shown) in which one or a plurality of signal lines are gathered.

The cable assembly contains signal lines for exchanging signals between the endoscope 1 and the light-source portion 3 and the processor portion 5, including a signal line for exchanging setting data, a signal line for exchanging image signals, a signal line for exchanging driving timing signals for driving the imaging device 31, and so forth.

In addition, as shown in FIGS. 2 and 3, the endoscope 1 is provided with: an image-acquisition optical system 29; the imaging device 31; an A/D converting portion 33; a compatibility-detection processing portion (compatibility-detecting portion) 35; an output-format switching portion 37; a Bayer-conversion processing portion (conversion processing portion) 39; an image-acquisition-information storing portion 41; and an illumination lens 43.

The image-acquisition optical system 29 is provided in the distal-end portion 15 of the inserted portion 9, and collects at least light coming from an observation site. The image-acquisition optical system 29 is configured by employing one or a plurality of lenses. The image-acquisition optical system 29 may be provided with an optical zooming mechanism for changing the angle of view and a focusing mechanism for changing focus.

The imaging device 31 is vertically disposed with respect to the optical axis of the image-acquisition optical system 29, and generates image signals (electrical signals, image information) by photoelectrically converting the light image formed by the image-acquisition optical system 29. The imaging device 31 is realized by employing a CCD (Charge Coupled Device) image sensor, a CMOS (Complementary Metal Oxide Semiconductor) image sensor, or the like.

Figure 4:
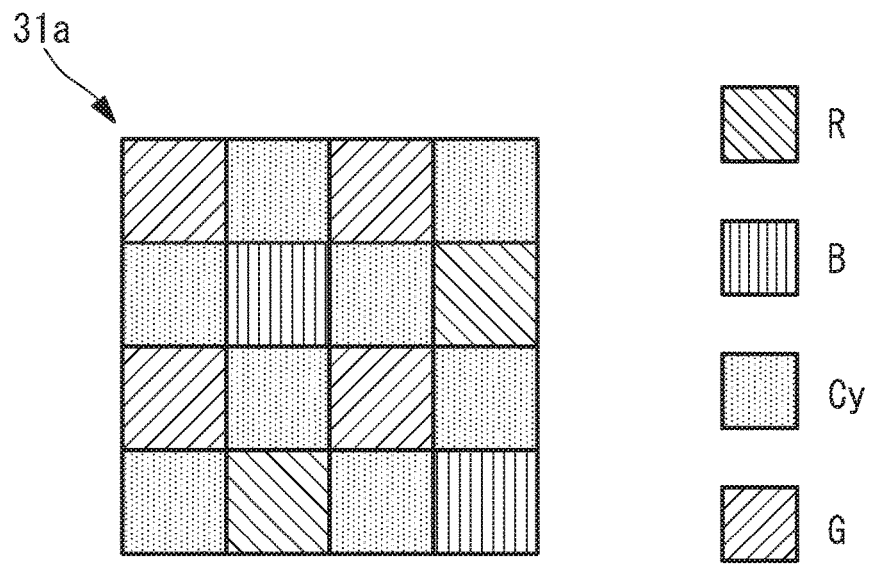
FIG. 4 is a diagram showing an example of a color filter.

A color filter 31a shown in FIGS. 3 and 4 is disposed on each of the pixels forming the imaging device 31.

The color filter 31a has, for example, a filter arrangement having R-pixels, G-pixels, and B-pixels, which are primary-color pixels, and Cy-pixels, which are complementary-color pixels. In the example in FIG. 4, the Cy-pixels are disposed in a checkered pattern at a proportion of ½ with respect to the entire filter, the G-pixels are disposed at a proportion of ¼ with respect to the entire filter, and the B-pixels and the R-pixels are disposed at a proportion of ⅛ each with respect to the entire filter.

Figure 5:
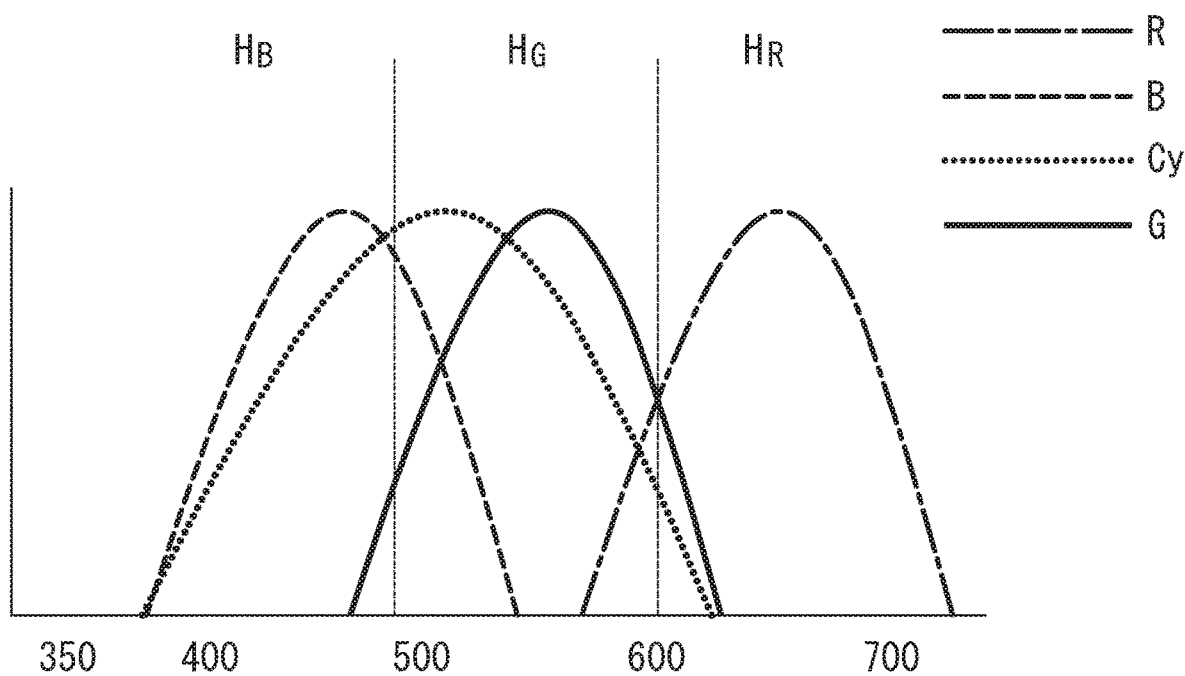
FIG. 5 is a graph showing an example of spectral characteristics of an imaging device.

In addition, the imaging device 31 exhibits, for example, spectral characteristics shown in FIG. 5. The B-pixels possess sensitivity in a blue wavelength band $H_B$, the G-pixels possess sensitivity in a green wavelength band $H_G$, the R-pixels possess sensitivity in a red wavelength band $H_R$, and the Cy-pixels possess sensitivity in the blue wavelength band $H_B$ and the green wavelength band $H_G$.

The A/D converting portion 33 converts the analog-format image signals generated by the imaging device 31 to digital-format image data, and outputs the converted image data to the output-format switching portion 37.

The compatibility-detection processing portion 35 detects whether or not the image-processing portion 63 of the processor portion 5 is compatible with the image information consisting of an array in which the primary-color pixels and the complementary-color pixels coexist depending on the color filter 31a, in other words, whether or not the image-processing portion 63 is capable of performing processing that is compatible with the filter arrangement of the imaging device 31, and outputs the detected signals to the output-format switching portion 37.

The output-format switching portion 37 directly outputs the image data received from the A/D converting portion 33 to the processor portion 5 in the case in which the result of the compatibility detection result by the compatibility-detection processing portion 35 indicates that the image-processing portion 63 is compatible, and outputs the image data received from the A/D converting portion 33 to the Bayer-conversion processing portion 39 in the case in which the image-processing portion 63 is not compatible.

The Bayer-conversion processing portion 39 converts the image data, which are based on the filter arrangement of the imaging device 31 and transmitted thereto from the output-format switching portion 37, to the Bayer array by applying Bayer-conversion processing thereto, and outputs the converted image data to the processor portion 5.

The light guide 27 is formed by using a glass fiber or the like, and guides the light emitted from the light-source portion 3.

The illumination lens 43 is disposed in the vicinity of the light guide 27, spreads out the light guided thereto through the light guide 27, and emits the light to the exterior of the distal-end portion 15.

The image-acquisition-information storing portion 41 stores various types of programs for operating the endoscope 1, various types of parameters required to operate the endoscope 1, and data including identification information and so forth of the endoscope 1. In addition, as shown in FIG. 3, the image-acquisition-information storing portion 41 has an identification-information storing portion 45 that stores the identification information. The identification information includes unique information (ID), model year, specification information, the transmission system of the endoscope 1, array information of the filter related to the color filter 31a (filter array information), and so forth. The image-acquisition-information storing portion 41 is realized by employing a flash memory or the like.

As shown in FIG. 3, the light-source portion 3 is provided with an illuminating portion 47 and an illumination-controlling portion 49.

The illuminating portion 47 emits one of a plurality of illumination light beams, which have different wavelength bands from each other, by switching among the light beams by means of control performed by the illumination-controlling portion 49. The illuminating portion 47 is provided with: a light source 51; a light-source driver 53; a switching filter 55, a driving portion 57; a driving driver 59; and a focusing lens 61.

The light source 51 emits white illumination light containing light in the red, green, and blue wavelength bands $H_B$, $H_G$, and $H_R$ by means of control performed by the illumination-controlling portion 49. The white illumination light emitted from the light source 51 is emitted to the exterior from the distal-end portion 15 of the inserted portion 9 via the switching filter 55, the focusing lens 61, and the light guide 27. The light source 51 is realized by employing a light source that emits white light, such as a white LED, a xenon lamp, or the like.

The light-source driver 53 supplies an electric current to the light source 51 by means of control performed by the illumination-controlling portion 49 and causes the white illumination light to be emitted from the light source 51.

The switching filter 55 allows only blue narrow-band light and green narrow-band light of the white illumination light emitted from the light source 51 to pass therethrough. In addition, the switching filter 55 is disposed, by means of control performed by the illumination-controlling portion 49, in the optical path of the white illumination light emitted from the light source 51 in a manner that allows insertion into the optical path and removal from the optical path.

As a result of being disposed in the optical path of the white illumination light, the switching filter 55 allows only the two types of the narrow-band light to pass therethrough. Specifically, the switching filter 55 allows narrow-band illumination light, which consists of light in a narrow band $T_B$ (for example, 390 to 445 nm) included in the wavelength band $H_B$ and light in a narrow band $T_G$ (for example, 530 to 550 nm) included in the wavelength band $H_G$, to pass therethrough.

The narrow bands $T_B$ and $T_G$ respectively correspond to blue light and green light that tend to be absorbed by hemoglobin in blood. So long as at least a bandwidth of 405 to 425 nm is included, any bandwidth is satisfactory as the narrow-band $T_B$. The light that is emitted limited to this bandwidth is referred to as narrow-band illumination light, and image observation performed by using narrow-band illumination is referred to as the narrow-band light observation (NBI) system.

The driving portion 57 is formed of a stepping motor, a DC motor, or the like, and inserts/removes the switching filter 55 into/from the optical path of the light source.

The driving driver 59 supplies a predetermined electric current to the driving portion 57 by means of control performed by the illumination-controlling portion 49.

The focusing lens 61 focuses the white illumination light emitted from the light source 51 or the narrow-band illumination light emitted from the switching filter 55, and emits the light to the exterior (the light guide 27) of the light-source portion 3.

The illumination-controlling portion 49 controls the type (bandwidth) of the illumination light to be emitted from the illuminating portion 47 by causing, by means of the light-source driver 53, the light source 51 to perform ON/OFF operations and by performing, by means of the driving driver 59, the insertion/removal operation of the switching filter 55 with respect to the optical path of the light source 51.

Specifically, by inserting/removing the switching filter 55 with respect to the optical path of the light source 51, the illumination-controlling portion 49 performs control for changing the illumination light to be emitted from the illuminating portion 47 to one of the white illumination light beam and the narrow-band illumination light beam. In other words, the illumination-controlling portion 49 performs control for changing the observation system to one of the white illumination light observation (WLI) system, in which the illumination light containing light in the wavelength bands $H_B$, $H_G$, and $H_R$ is employed, and the narrow-band light observation (NBI) system, in which the narrow-band illumination light consisting of the light in the narrow bands $T_B$ and $T_G$ is employed.

The processor portion 5 is provided with: the image-processing portion 63; and an inputting portion 65; a storing portion 67; and a controlling portion 69.

The image-processing portion 63 executes predetermined image processing on the image data transmitted thereto from the endoscope 1 and generates display image signals to be displayed by the display portion 7. As the image processing, in addition to the demosaicing processing, OB clamping processing, gain adjustment, and so forth are performed. In the OB clamping processing, processing for correcting an offset quantity of the black level is applied to the image data input from the endoscope 1. In gain adjustment processing, processing for adjusting the brightness level is applied to the image data to which the demosaicing processing has been applied.

The inputting portion 65 is an interface for a user to perform input or the like with respect to the processor portion 5. The inputting portion 65 is configured to include a power switch for turning the power ON/OFF, a mode-switching button for changing the image-capturing mode and various types of other modes, an illumination-light switching button for changing the type of the illumination light of the light-source portion 3, and so forth.

The storing portion 67 stores various types of programs for operating the endoscope apparatus 101 and data including various types of parameters required to operate the endoscope apparatus 101. In addition, the storing portion 67 stores the information related to the endoscope 1, for example, a table about the relationship between the unique information (ID) related to the endoscope 1 and the information related to the filter arrangement of the color filters 31a (a compatible-filter table of the image-processing portion 63) or the like. The storing portion 67 is realized by employing a semiconductor memory, such as a flash memory, a DRAM (Dynamic Random Access Memory), or the like.

The controlling portion 69 is configured by employing a CPU or the like, and performs drive control of the individual constituent portions including the endoscope 1 and the light-source portion 3, as well as information input/output control with respect to the individual constituent portions. In addition, the controlling portion 69 transmits, to the endoscope 1, setting data (for example, pixels to be loaded or the like) which are for image-acquisition control and stored in the storing portion 67, timing signals related to the image-acquisition timing, and so forth via the predetermined signal lines.

The display portion 7 receives the display image signals generated by the processor portion 5 via a video cable, and displays the body-interior image corresponding to the received display image signals. The display portion 7 is configured by employing liquid crystals or organic EL (Electro Luminescence).

The operation of the endoscope apparatus 101 thus configured will be described with reference to the flowchart in FIG. 6.

In order to generate an observation image by means of the endoscope apparatus 101 according to this embodiment, first, the endoscope 1 is connected to the processor portion 5. Once the preparation for starting image acquisition is completed, the compatibility-detection processing portion 35 detects whether or not it is possible for the image-processing portion 63 to perform processing that is compatible with the filter arrangement of the imaging device 31 (step SA1).

Figure 7:
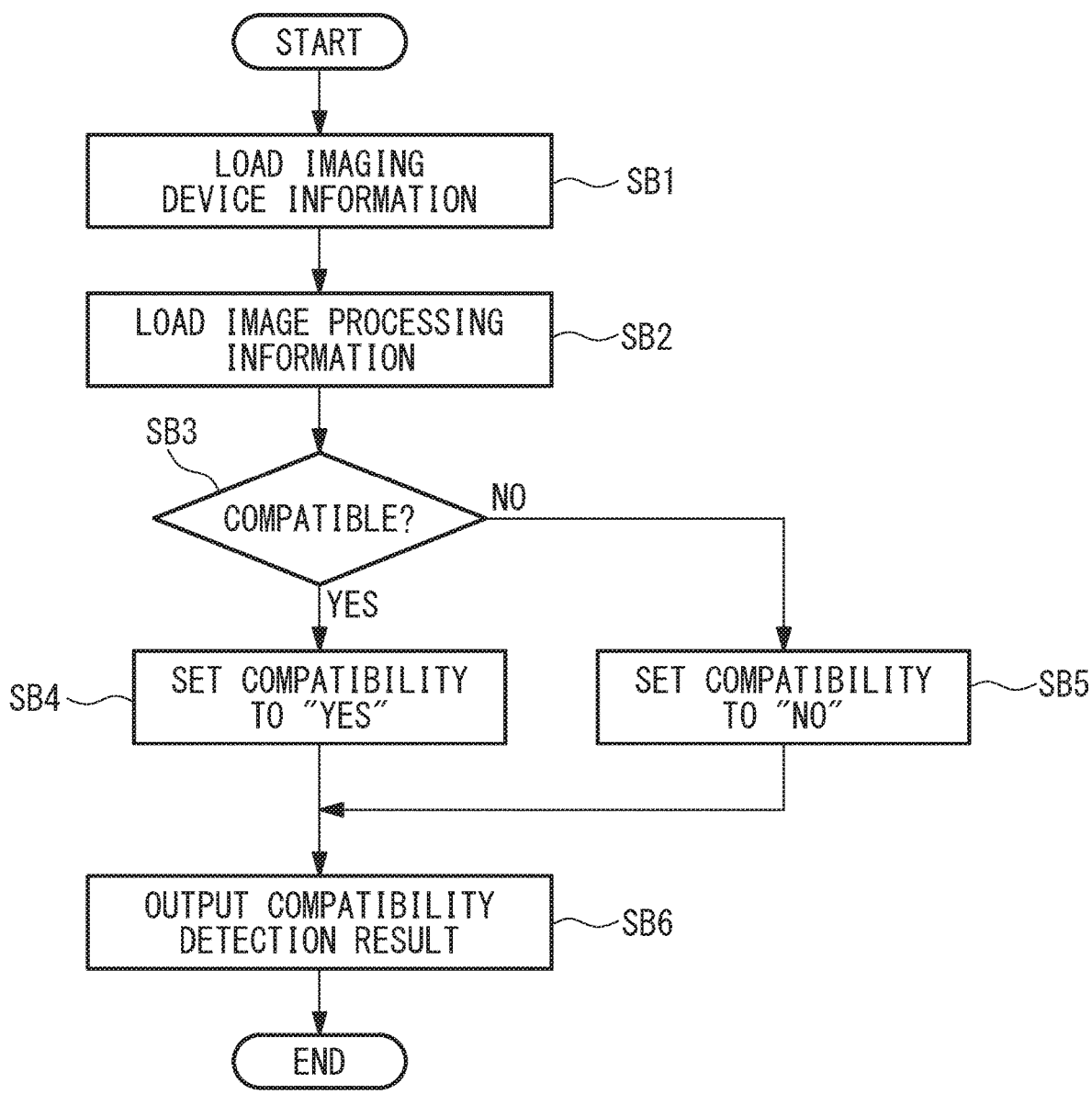
FIG. 7 is a flowchart for explaining compatibility-detection processing in the flowchart in FIG. 6.

Here, the compatibility-detection processing in the step SA1 will be described with reference to the flowchart in FIG. 7.

First, the compatibility-detection processing portion 35 loads the information about the filter arrangement of the imaging device 31, which is stored in the identification-information storing portion 45 of the endoscope 1 (step SB1), loads the compatible-filter table of the image-processing portion 63, which is stored in the storing portion 67 (step SB2), and compares these information items (step SB3).

Next, in the case in which the compatibility-detection processing portion 35 detects that the endoscope 1 and the processor portion 5 are compatible with each other, compatibility is set to "YES" (step SB4), in the case in which the compatibility-detection processing portion 35 detects that the endoscope 1 and the processor portion 5 are not compatible with each other, compatibility is set to "NO" (step SB5), and these compatibility detection results are output to the output-format switching portion 37 (step SB6).

Figure 6:
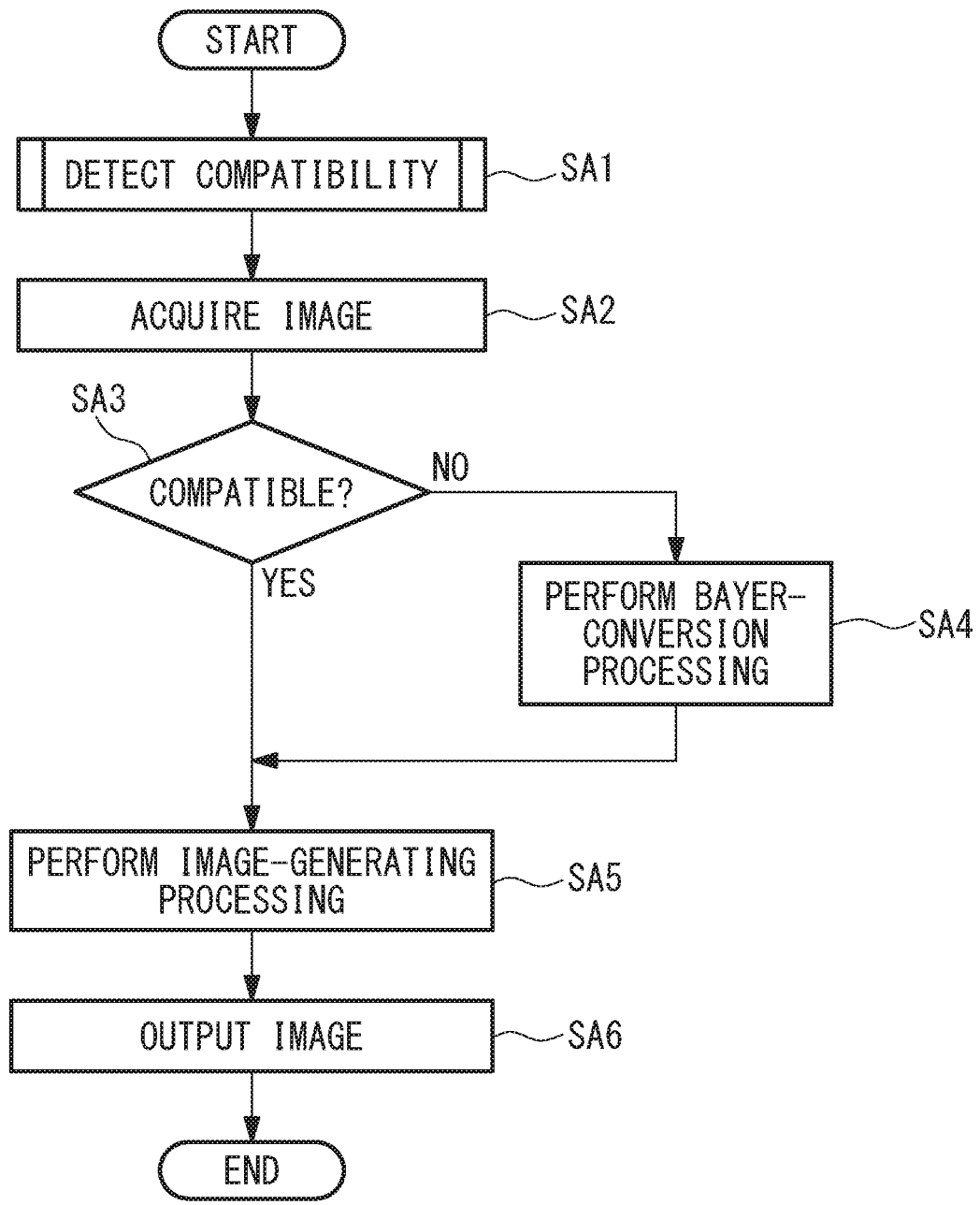
FIG. 6 is a flowchart for explaining a method for generating an observation image by means of the endoscope apparatus in FIG. 1.

Returning to the flowchart in FIG. 6, image acquisition of the imaging subject is started (step SA2). The subject is irradiated with the illumination light from the light-source portion 3, the imaging device 31 of the endoscope 1 acquires an image of the imaging subject, the image-processing portion 63 of the processor portion 5 applies various types of signal processing to the image data acquired by the imaging device 31, and thus, a color image is generated.

Next, the output-format switching portion 37 changes the output format in accordance with the compatibility result detected by the compatibility-detection processing portion 35 (step SA3). Specifically, in the case in which compatibility is set to "YES" by the compatibility-detection processing portion 35, the output-format switching portion 37 directly outputs the image data acquired by the imaging device 31 in the step SA2 to the processor portion 5.

On the other hand, in the case in which compatibility is set to "NO" by the compatibility-detection processing portion 35, the output-format switching portion 37 outputs the image data acquired by the imaging device 31 in the step SA2 to the Bayer-conversion processing portion 39 (step SA4). Then, the Bayer-conversion processing portion 39 converts, to the primary-color Bayer array, the image data of the filter arrangement of the imaging device 31, in which the primary-color pixels and the complementary-color pixels coexist.

Figure 8:
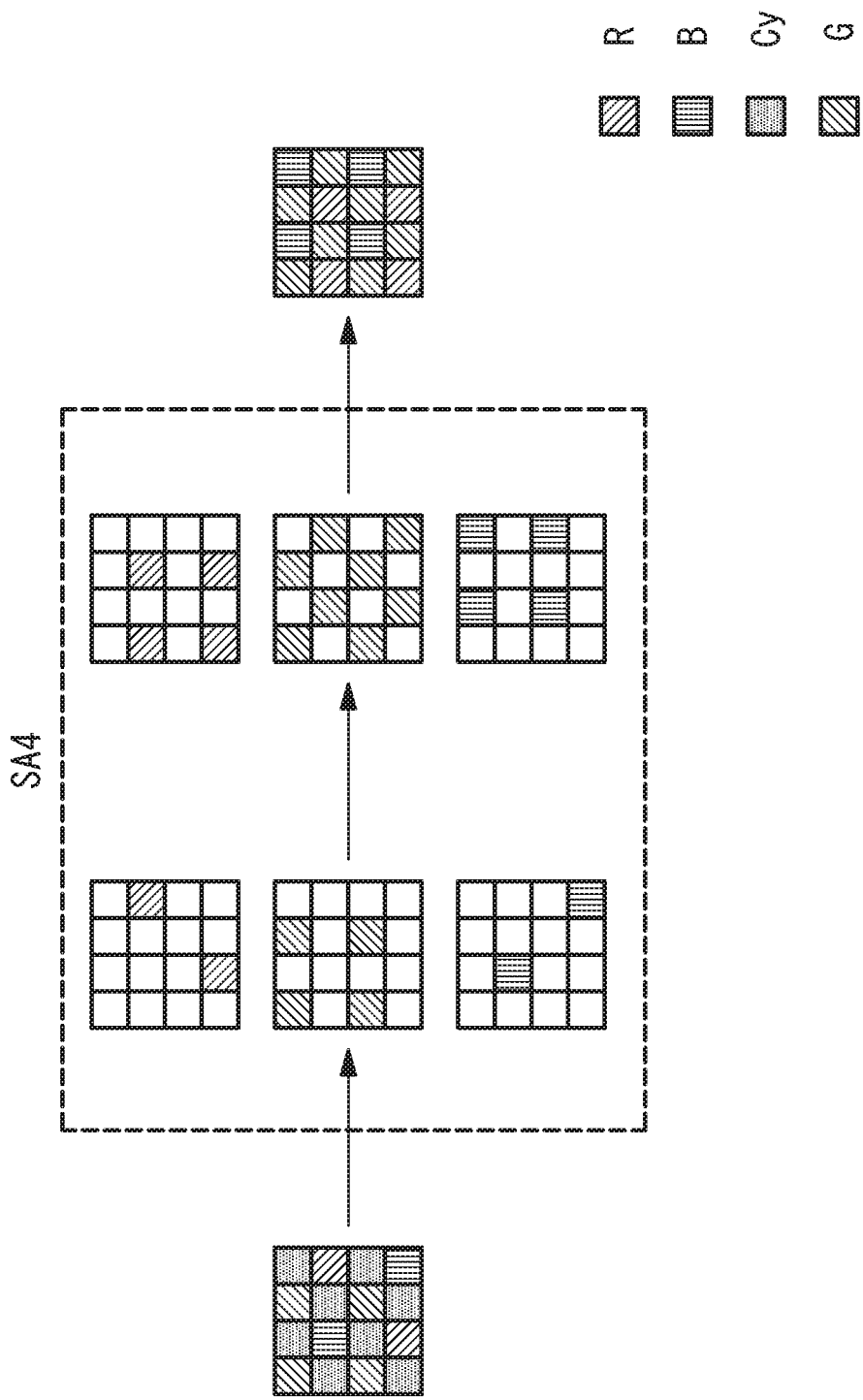
FIG. 8 is a diagram for explaining Bayer-conversion processing of image data performed by the endoscope apparatus FIG. 1.

For example, as shown in FIG. 8, pixel values acquired by the imaging device 31 are used, and the image data are converted to primary-color Bayer array data by means of interpolation processing. In FIG. 8, the G-pixels disposed at a proportion of ¼ with respect to the entire filter are interpolated so as to account for ½ of the entire filter, and the R-pixels and the B-pixels disposed at a proportion of ⅛ each with respect to the entire filter are interpolated so as to account for ¼ each with respect to the entire filter, and thus, conversion to the Bayer array is completed. It is possible to realize the interpolation processing by employing existing processing, and it is possible to employ, for example, bilinear interpolation, cubic interpolation, direction discrimination interpolation, and so forth. The image data converted by the Bayer-conversion processing portion 39 are output to the processor portion 5.

In the processor portion 5, the image-processing portion 63 applies various types of image processing to the image data transmitted thereto from the endoscope 1, thus generating the display image signals (step SA5). The display image signals generated by the image-processing portion 63 are transmitted to the display portion 7, and a body-interior image corresponding to the display image signals is displayed on the display portion 7 (step SA6).

As has been described above, with the endoscope apparatus 101 provided with the endoscope 1 according to this embodiment, it is possible to change the output format of the endoscope 1 in accordance with the combination of the imaging device 31 and the image-processing portion 63. Therefore, when acquiring an image by using an imaging device 31 having a filter arrangement in which the primary-color pixels and the complementary-color pixels coexist, it is possible to obtain a desired output image both in the case in which the image-processing portion 63 is compatible with the imaging device 31 and in the case in which the image-processing portion 63 is compatible only with the primary-color Bayer array.

Also, with the endoscope 1 according to this embodiment, even in the case in which the image-processing portion 63 is compatible only with the primary-color Bayer array, it is possible to precisely generate an observation image by means of the image-processing portion 63 for Bayer-processing regardless of the filter array of the imaging device 31 without having to improve the image-processing portion 63 for Bayer-processing.

It is possible to modify the endoscope 1 according this embodiment as below.

Figure 9:
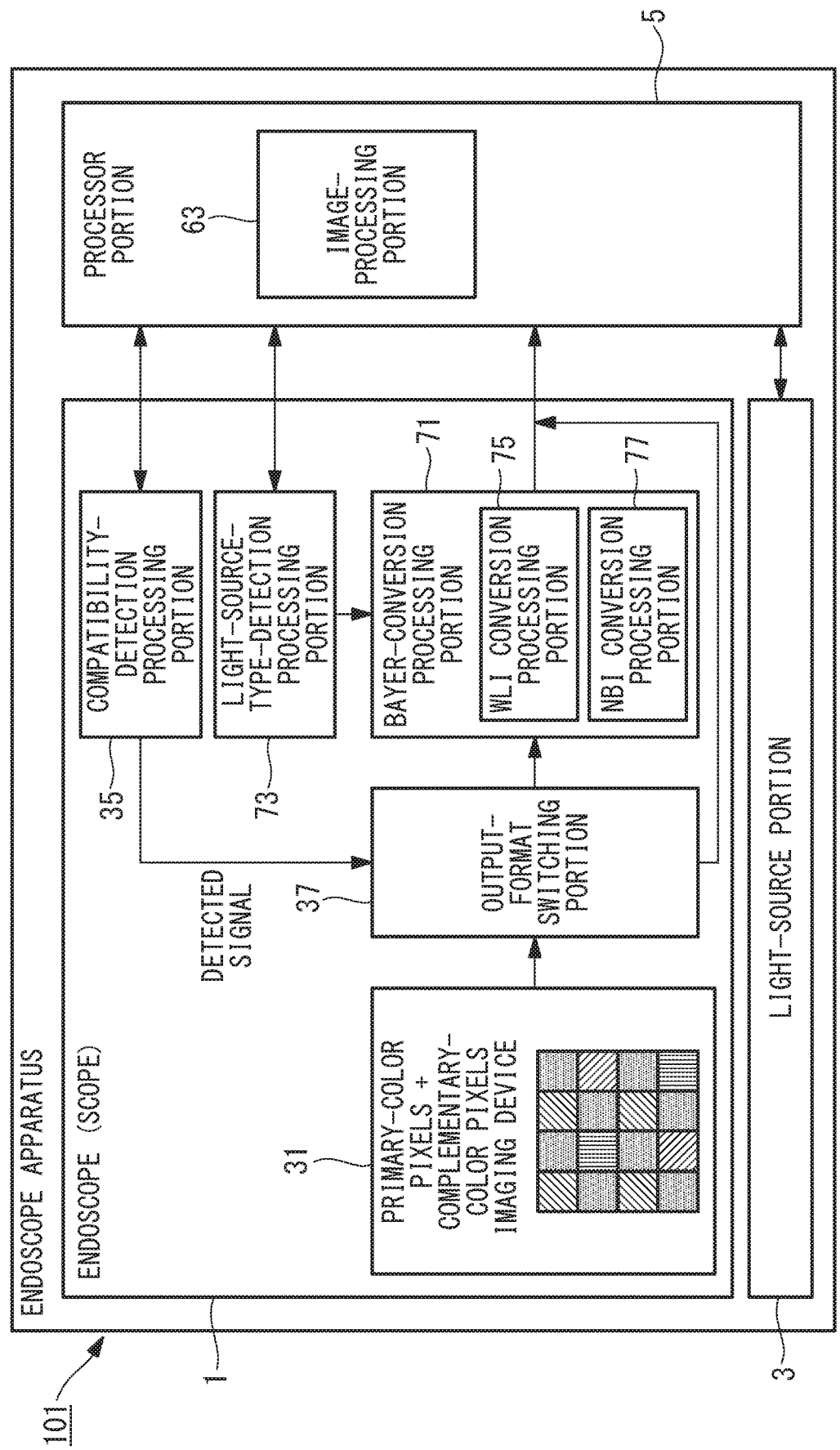
FIG. 9 is a block diagram showing the configuration of an endoscope apparatus according to a modification of the first embodiment of the present invention.

For example, as shown in FIG. 9, the endoscope 1 may be provided with, instead of the Bayer-conversion processing portion 39, a Bayer-conversion processing portion 71 that changes the specifics of the Bayer-conversion processing in accordance with the type of the light-source portion 3, and the endoscope 1 may additionally be provided with a light-source-type-detection processing portion (light-source-type-detecting portion) 73 that detects whether or not the illumination light is one of the white illumination light beam and the narrow band illumination light beam, in other words, whether or not the type of the light-source portion 3 is one of that for the WLI system and that for the NBI system.

In addition, the Bayer-conversion processing portion 71 may be provided with: a WLI conversion processing portion 75 that converts the image data to a Bayer array in which the G-pixels are in a checkered pattern in the case in which the illumination light is the white illumination light, in other words, in the case in which the light-source-type-detection processing portion 73 detects that the light-source portion 3 is for the WLI system; and an NBI conversion processing portion 77 that converts the image data to a Bayer array in which the Cy-pixels are in a checkered pattern in the case in which the illumination light is the narrow band illumination light, in other words, in the case in which the light-sourcetype-detection processing portion 73 detects that the light-source portion 3 is for the NBI system.

Figure 10:
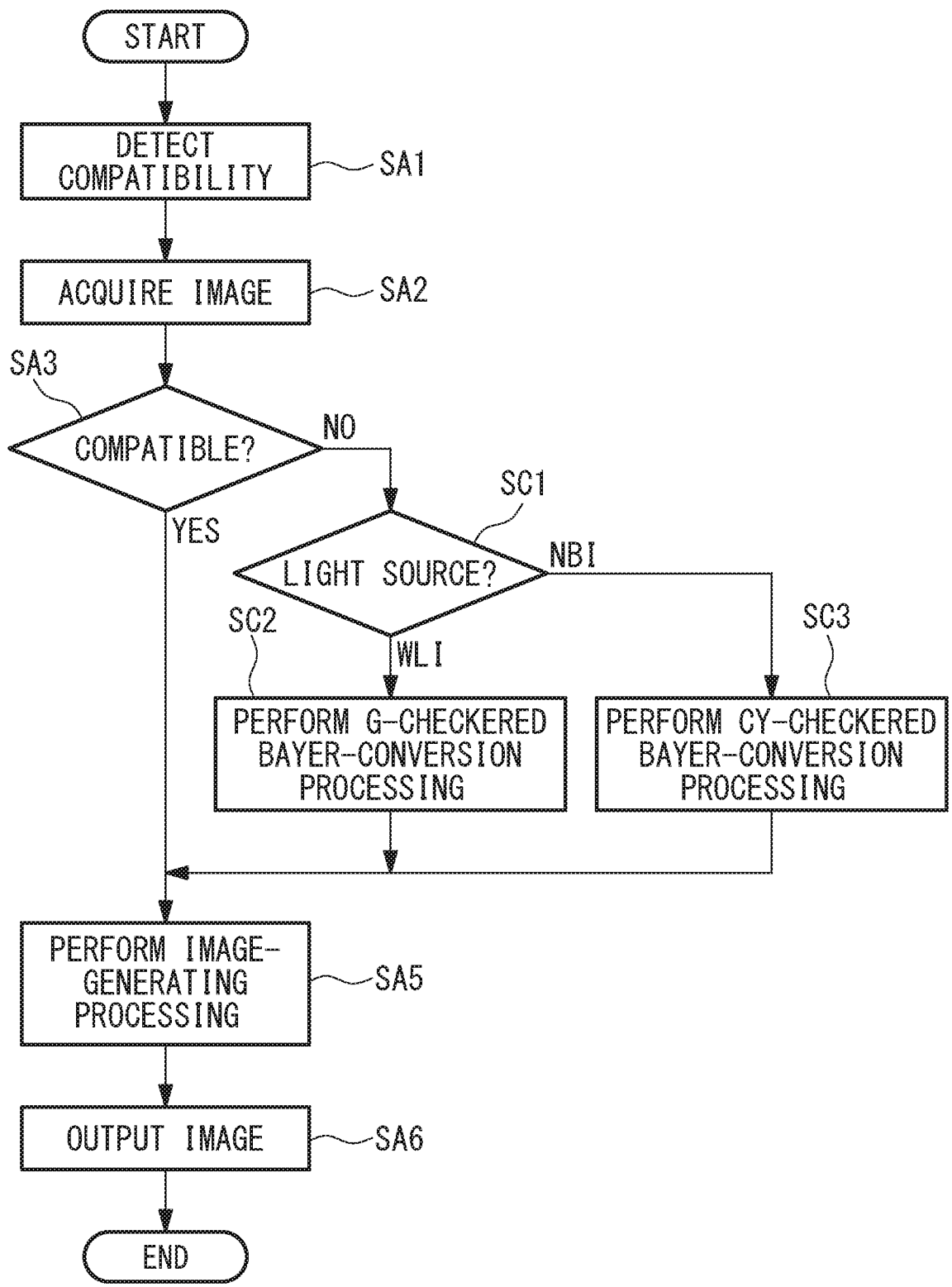
FIG. 10 is a flowchart for explaining a method for generating an observation image by means of the endoscope apparatus in FIG. 9.

In this case, as shown in the flowchart in FIG. 10, in the case in which the compatibility-detection processing portion 35 detects that the image-processing portion 63 is not compatible with the filter arrangement of the imaging device 31 in the step SA3, the type of the light-source portion 3 is detected by the light-source-type-detection processing portion 73 (step SC1).

Figure 11:
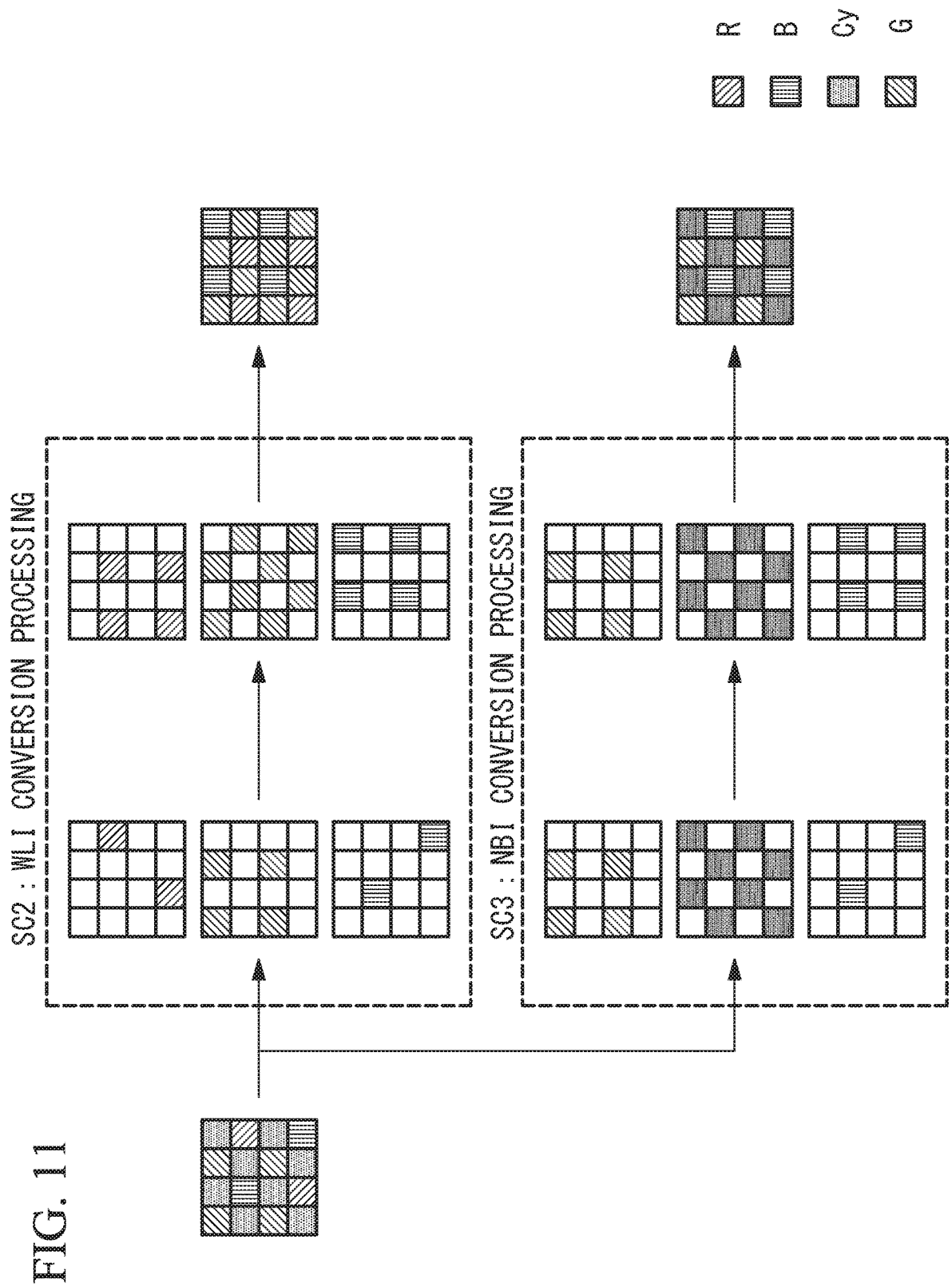
FIG. 11 is a diagram for explaining Bayer-conversion processing of image data performed by the endoscope apparatus in FIG. 9.

Also, in the case in which the light-source-type-detection processing portion 73 detects that the light-source portion 3 is for the WLI system, the WLI conversion processing portion 75 performs the conversion to the Bayer array in which the G-pixels of the image data acquired by the imaging device 31 in the step SA2 are in a checkered pattern (step SC2, WLI conversion processing). As shown in FIG. 11, the WLI conversion processing is the same as the processing in the first embodiment shown in FIG. 8.

On the other hand, in the case in which the light-source-type-detection processing portion 73 detects that the light-source portion 3 is for the NBI system, the NBI conversion processing portion 77 performs the conversion to the Bayer array in which the Cy-pixels of the image data acquired by the imaging device 31 in the step SA2 are in a checkered pattern (step SC3, NBI conversion processing).

In the NBI conversion processing shown in FIG. 11, the Cy-pixels remain in the checkered pattern, and the B-pixels in the positions of the R-pixels are determined by means of interpolation processing. In the image data to be output, the Bayer array thereof is such that, although colors are different from the primary-color RGB, one color is disposed in a checkered pattern and the remaining two colors are disposed at a density of ¼ each with respect to the entire filter.

In the case of the NBI system, because the B narrow band light and the G narrow band light are radiated, it is not possible to acquire information at the R-pixels. Because of this, in the case of the NBI conversion processing, the conversion is made to Bayer array data consisting of the Cy-pixels, the G-pixels, and the B-pixels excluding the R-pixels.

The image data to which the WLI conversion processing portion 75 has applied the Bayer conversion and the image data to which the NBI conversion processing portion 77 has applied to the Bayer conversion are transmitted to the processor portion 5. In the processor portion 5, the image-processing portion 63 applies various types of image processing to the image data transmitted thereto from the endoscope 1, thus generating the display image signals (step SA5).

For example, in the case of the WLI system, a correlation with the G-pixels disposed in a checkered pattern is utilized, and demosaicing processing for the B-pixels and the R-pixels is applied to the image data. In addition, in the case of the NBI system, a correlation with the Cy-pixels disposed in a checkered pattern is utilized, and demosaicing processing for the G-pixels and the B-pixels is applied to the image data.

In both cases, because the pixels serving as interpolation subjects (the B-pixels and the R-pixels in the WLI system and the G-pixels and the B-pixels in the NBI system) and the pixels in a checkered pattern (the G-pixels in the WLI system and the Cy-pixels in the NBI system) are highly correlated, it is possible to output a highly precise interpolated image making full use of the performance of demosaicing processing for the Bayer array.

With this modification, in addition to the effect of this embodiment, described above, it is possible to output an image having a high resolution regardless of the type of the observation system. In demosaicing processing for the Bayer array, highly precise interpolation processing is performed by using the correlation with the pixels disposed in a checkered pattern (the G-pixels in the primary-color Bayer array). As a result of performing the conversion so that the G-pixels, which are highly correlated with the B-pixels as well as the R-pixels, are disposed in a checkered pattern in the case of the WLI system, and performing the conversion so that the Cy-pixels, which are highly correlated with the B-pixels as well as the G-pixels, are disposed in a checkered pattern in the case of the NBI system, it is possible to generate a highly precise output image making full use of the performance of demosaicing processing for the Bayer array.

Second Embodiment

Next, an endoscope processor according to a second embodiment of the present invention will be described below with reference to the drawings.

Figure 12:
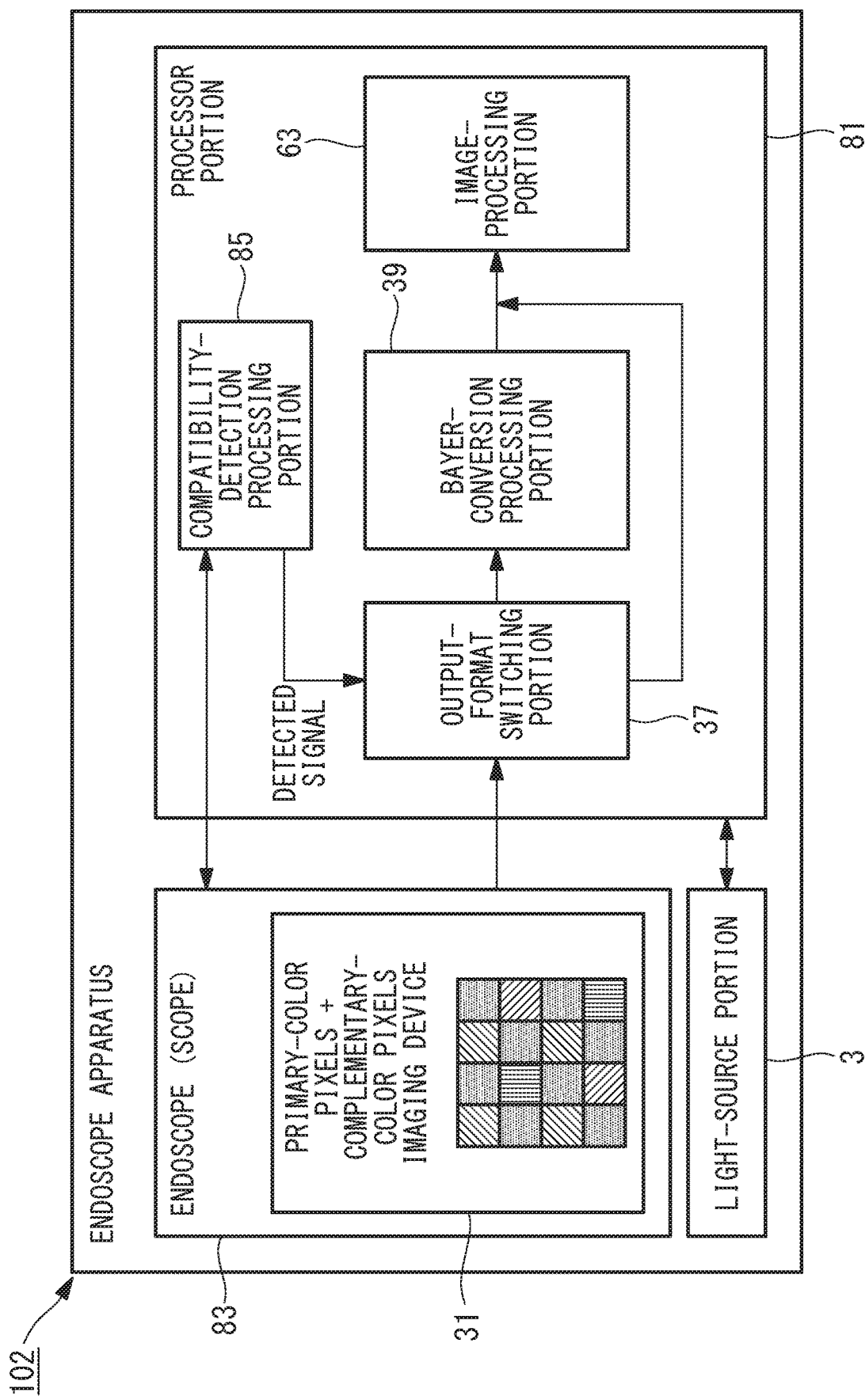
FIG. 12 is a block diagram showing the configuration of an endoscope apparatus according to a second embodiment of the present invention.

A processor portion (endoscope processor) 81 according to this embodiment is employed in, for example, an endoscope apparatus 102 shown in FIG. 12.

The endoscope apparatus 102 differs from the first embodiment in that an endoscope 83 that is not provided with the compatibility-detection processing portion 35, the output-format switching portion 37, and the Bayer-conversion processing portion 39 is employed instead of the endoscope 1, and a processor portion 81 is provided with a compatibility-detection processing portion (array-detecting portion) 85, the output-format switching portion 37, and the Bayer-conversion processing portion 39.

In describing this embodiment, portions having the same configurations as those in the endoscope apparatus 101 according to the first embodiment, described above, are given the same reference signs, and the descriptions thereof will be omitted.

The compatibility-detection processing portion 85 detects whether or not the image data output from the imaging device 31 of the endoscope 83 connected to the processor portion 81 consist of the Bayer array, in other words, whether or not the filter arrangement of the imaging device 31 is compatible with processing performed by the image-processing portion 63 of the processor portion 81.

The image-processing portion 63 of this embodiment is compatible only with the primary-color Bayer array.

The operation of the endoscope apparatus 102 thus configured will be described.

When the endoscope 83 is connected to the processor portion 81, the compatibility-detection processing portion 85 detects that the endoscope 83 is not compatible with the processor portion 81, and compatibility is set to "NO" (step SB5), and the compatibility detection result is output to the output-format switching portion 37 (step SB6).

Next, in accordance with the compatibility result detected by the compatibility-detection processing portion 85 (here, compatibility is set to "NO"), the output-format switching portion 37 outputs the image data acquired by the imaging device 31 in the step SA2 to the Bayer-conversion processing portion 39 (step SA4).

Then, the Bayer-conversion processing portion 39 converts, to the primary-color Bayer array, the image data of the filter arrangement of the imaging device 31, in which the primary-color pixels and the complementary-color pixels coexist. By doing so, in the image-processing portion 63, various types of image processing are applied to the image data that have been converted to the primary-color Bayer array, thus generating the display image signals (step SA5).

As has been described above, with the processor portion 81 according to this embodiment, it is possible to precisely generate, with the image-processing portion 63 for Bayer-processing, an observation image by means of the image-processing portion 63 for Bayer-processing regardless of the filter array of the imaging device 31 without having to improve the image-processing portion 63 for Bayer-processing.

In addition, the amount of processing performed in the endoscope 83 is reduced, and thus, it is possible to reduce the cost of the endoscope 83. Furthermore, because the size of a circuit substrate installed in the processor portion 81 is larger than that of the endoscope 83, it is possible to perform complicated processing, and it is possible to increase the precision of the processing performed by the Bayer-conversion processing portion 39.

It is also possible to modify the second embodiment in the same manner as in the modification of the first embodiment.

Specifically, the processor portion 81 may be provided with, instead of the Bayer-conversion processing portion 39, the Bayer-conversion processing portion 71 that changes the specifics of the Bayer-conversion processing in accordance with the type of the light-source portion 3, and the processor portion 81 may additionally be provided with the light-source-type-detection processing portion 73 that detects whether or not the illumination light is one of the white illumination light beam and the narrow band illumination light beam, in other words, whether or not the type of the light-source portion 3 is one of that for the WLI system and that for the NBI system.

In this case, in the case in which the compatibility-detection processing portion 85 detects that the filter arrangement of the imaging device 31 is not compatible with the image-processing portion 63 for Bayer-processing, the type of the light-source portion 3 may be detected by the light-source-type-detection processing portion 73.

Also, in the case in which the illumination light is the white illumination light, in other words, in the case in which the light-source-type-detection processing portion 73 detects that the light-source portion 3 is for the WLI system, the WLI conversion processing portion 75 may perform the conversion to the Bayer array in which the G-pixels in the image data acquired by the imaging device 31 in the step SA2 are in a checkered pattern. In addition, in the case in which the illumination light is the narrow band illumination light, in other words, in the case in which the light-source-type-detection processing portion 73 detects that that the light-source portion 3 is for the NBI system, the NBI conversion processing portion 77 may perform the conversion to the Bayer array in which the Cy-pixels in the image data acquired by the imaging device 31 in the step SA2 are in a checkered pattern.

With this modification also, it is possible to generate a highly precise output image making full use of the performance of demosaicing processing for the Bayer array, as with the modification of the first embodiment.

Third Embodiment

Next, an endoscope adaptor according to a third embodiment of the present invention will be described below with reference to the drawings.

Figure 13:
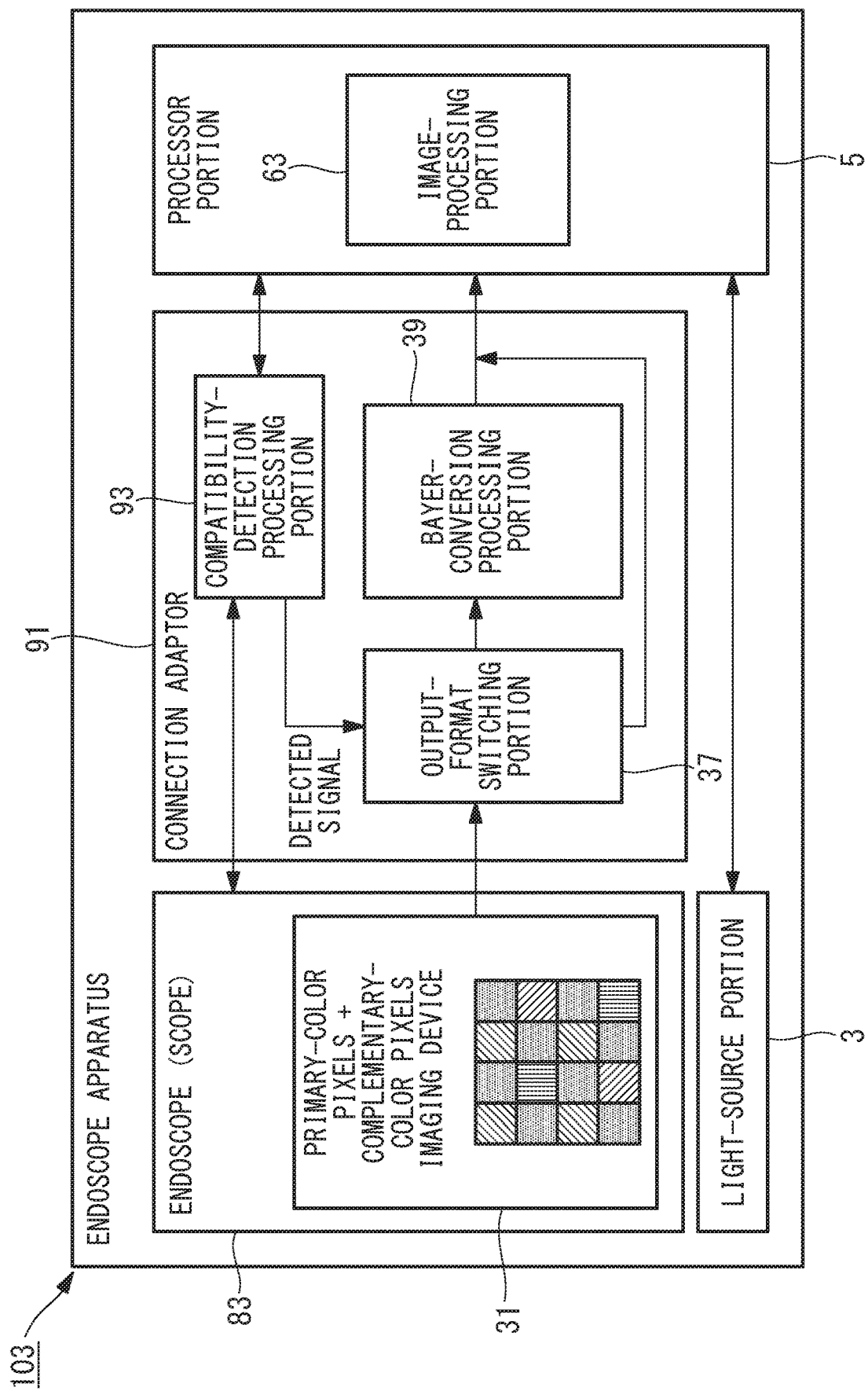
FIG. 13 is a block diagram showing the configuration of an endoscope apparatus according to a third embodiment of the present invention.

An endoscope adaptor 91 according to this embodiment is employed in, for example, an endoscope apparatus 103 as shown in FIG. 13, and is connected to the endoscope 83 and the processor portion 5.

The endoscope apparatus 103 differs from the first and second embodiments in that the endoscope adaptor 91 is provided with a compatibility-detection processing portion (array-detecting portion) 93, the output-format switching portion 37, and the Bayer-conversion processing portion 39.

In describing this embodiment, portions having the same configurations as those in the endoscope apparatuses 101 and 102 according to the first and second embodiments, described above, are given the same reference signs, and the descriptions thereof will be omitted.

The compatibility-detection processing portion 93 detects whether or not the image data output from the imaging device 31 of the endoscope 83 connected to the processor portion 5 consists of the Bayer array, in other words, whether or not the filter arrangement of the imaging device 31 of the endoscope 83 is compatible with the processing performed by the image-processing portion 63.

The operation of the endoscope apparatus 103 thus configured will be described.

In the case in which the compatibility-detection processing portion 93 detects that the endoscope 83 and the processor portion 5 are compatible with each other, compatibility is set to "YES" (step SB4), in the case in which the compatibility-detection processing portion 93 detects that the endoscope 83 and the processor portion 5 are not compatible with each other, compatibility is set to "NO" (step SB5), and these compatibility detection results are output to the output-format switching portion 37 (step SB6)

Next, in the case in which compatibility is set to "YES" by the compatibility-detection processing portion 93, the output-format switching portion 37 directly outputs the image data acquired by the imaging device 31 in the step SA2 to the processor portion 5, and, on the other hand, in the case in which compatibility is set to "NO" by the compatibility-detection processing portion 93, the output-format switching portion 37 outputs the image data acquired by the imaging device 31 in the step SA2 to the Bayer-conversion processing portion 39 (step SA4).

Then, the Bayer-conversion processing portion 39 converts, to the primary-color Bayer array, the image data based on the filter arrangement of the imaging device 31, in which the primary-color pixels and the complementary-color pixels coexist. In the processor portion 5, the image-processing portion 63 applies various types of image processing to the image data transmitted thereto from the endoscope 83, thus generating the display image signals (step SA5).

With the endoscope apparatus 103 provided with the endoscope adaptor 91 thus configured, it is possible to afford the same effect as that of the first embodiment without adding alterations to the endoscope 83 and the processor portion 5.

As has been described above, with the endoscope adaptor 91 according to this embodiment, even in the case in which the image-processing portion 63 is compatible only with the primary-color Bayer array, it is possible to precisely generate an observation image by means of the image-processing portion 63 for Bayer-processing regardless of the filter array of the imaging device 31 without having to improve the image-processing portion 63 for Bayer-processing. In addition, with the endoscope apparatus 103 provided with the endoscope adaptor 91 such as that above, it is possible to afford the same effect as that of the first embodiment without making alterations to the endoscope 83 and the processor portion 5.

It is also possible to modify the third embodiment in the same manner as in the modification of the first embodiment.

Specifically, the processor portion 5 may be provided with, instead of the Bayer-conversion processing portion 39, the Bayer-conversion processing portion 71 that changes the specifics of the Bayer-conversion processing in accordance with the type of the light-source portion 3, and the processor portion 5 may additionally be provided with the light-source-type-detection processing portion 73 that detects whether or not the illumination light is one of the white illumination light beam and the narrow band illumination light beam, in other words, whether or not the type of the light-source portion 3 is one of that for the WLI system and that for the NBI system.

In this case, in the case in which the compatibility-detection processing portion 35 detects that the filter arrangement of the imaging device 31 is not compatible with the processing performed by the image-processing portion 63, the type of the light-source portion 3 may be detected by the light-source-type-detection processing portion 73.

Also, in the case in which the illumination light is the white illumination light, in other words, in the case in which the light-source-type-detection processing portion 73 detects that the light-source portion 3 is for the WLI system, the WLI conversion processing portion 75 may perform the conversion to the Bayer array in which the G-pixels in the image data acquired by the imaging device 31 in the step SA2 are in a checkered pattern. In addition, in the case in which the illumination light is the narrow band illumination light, in other words, in the case in which the light-source-type-detection processing portion 73 detects that that the light-source portion 3 is for the NBI system, the NBI conversion processing portion 77 may perform the conversion to the Bayer array in which the Cy-pixels in the image data acquired by the imaging device 31 in the step SA2 are in a checkered pattern.

With this modification also, it is possible to generate a highly precise output image making full use of the performance of demosaicing processing for the Bayer array, as with the modification of the first embodiment and the modification of the second embodiment.

It is possible to modify the above-described individual embodiments, as described below.

Although the individual embodiments, described above, have been described by using the color filter 31*a* shown in FIG. 4, the color filter arrangement is not limited thereto, so long as a filter arrangement in which the primary-color pixels and the complementary-color pixels coexist is employed. For example, as a first modification, a color filter 31*b* having the filter arrangement shown in FIG. 14 may be employed.

In the filter arrangement shown in FIG. 14, the R-pixels in the filter arrangement in FIG. 4 are replaced with complementary-color MG-pixels. The MG-pixels possess sensitivity for each of the blue wavelength band $H_B$ and the red wavelength band $H_R$.

The imaging device 31 exhibits, for example, spectral characteristics shown in FIG. 15.

Figure 16:
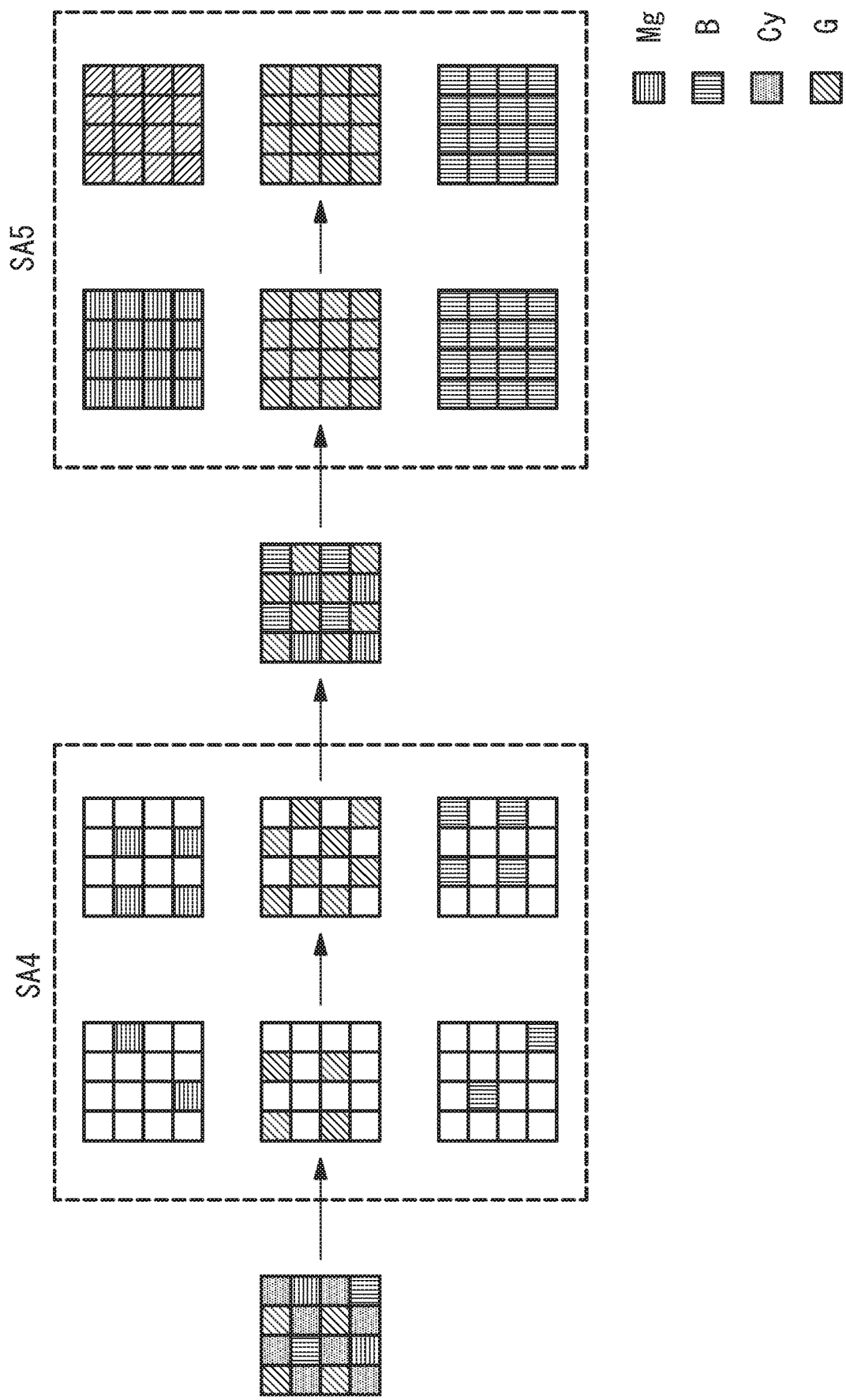
FIG. 16 is a diagram for explaining Bayer-conversion processing of image data performed by the color filter in FIG. 14.

In the case of the filter arrangement shown in FIG. 14, when converted to the Bayer array by the Bayer-conversion processing portion 39, the image data becomes a Bayer array containing the complementary-color Mg. At this time, when the output image is generated by the image-processing portion 63, the R-pixels are generated by means of color conversion processing. In FIG. 16, although R-information is generated by means of the color conversion processing after performing the demosaicing processing, naturally, the demosaicing processing may be performed after performing color conversion for only the positions of the MG-pixels before performing demosaicing.

By doing so, because parameters for the color conversion processing are often externally input, it is possible to achieve the effects afforded by the individual embodiments, described above, without altering the processing circuit of the processor portion 5 even in the case in which the MG-pixels are contained.

Figure 17:
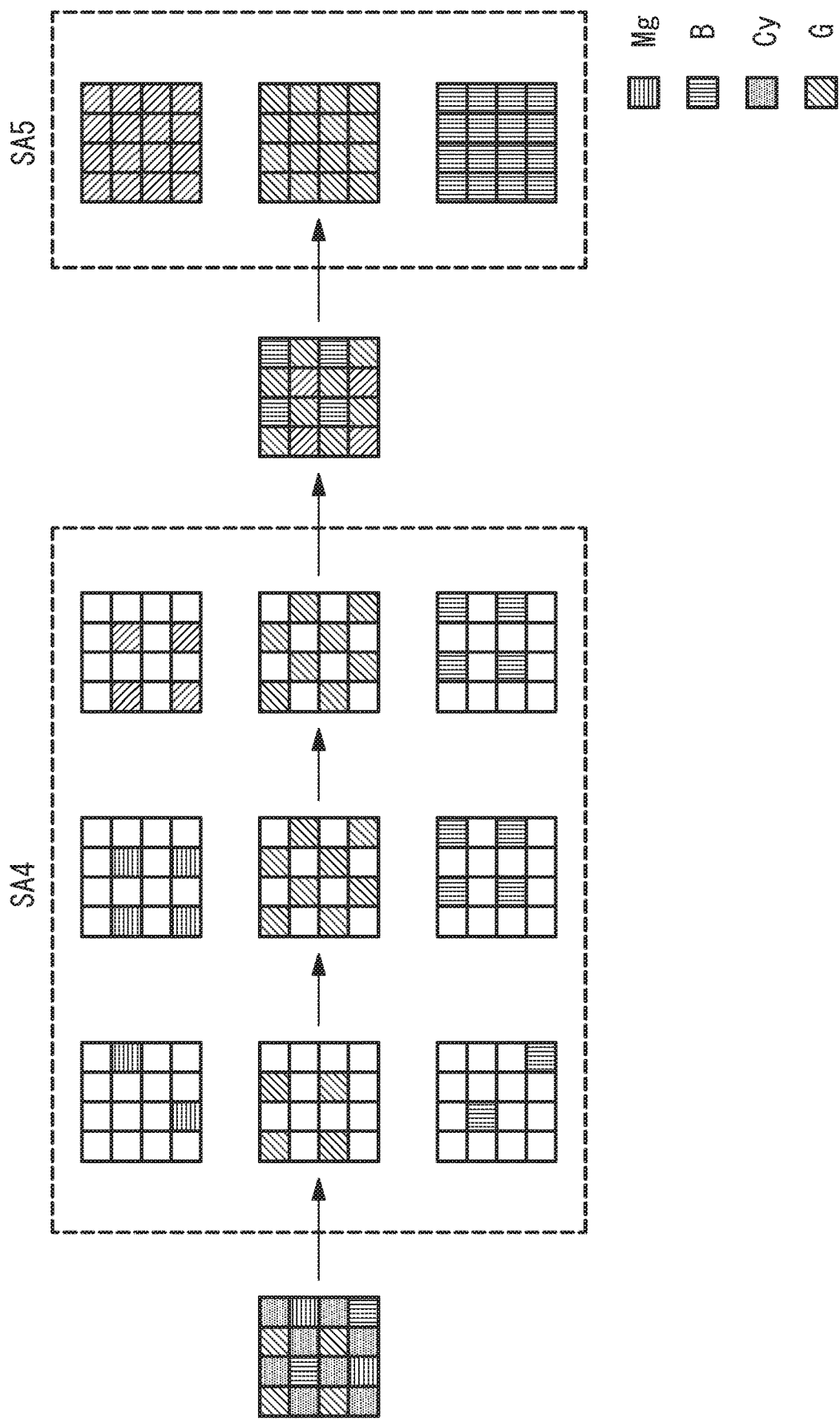
FIG. 17 is a diagram for explaining an example of Bayer-conversion processing, which is a second modification of the individual embodiments of the present invention.

In addition, as a second modification, as shown in FIG. 17, processing up to the color conversion processing may be performed by means of the Bayer-conversion processing portion 39, and the image data may be output after converting the image data to a Bayer array containing only the primary-color pixels.

By doing so, even in the case in which the MG-pixels are contained, it is possible to achieve the effects afforded by the individual embodiments, described above, without altering anything about the processor portion 5 including the parameters. In other words, it is possible to generate a highly precise observation image making full use of the performance of demosaicing processing for the Bayer array.

Figure 18:
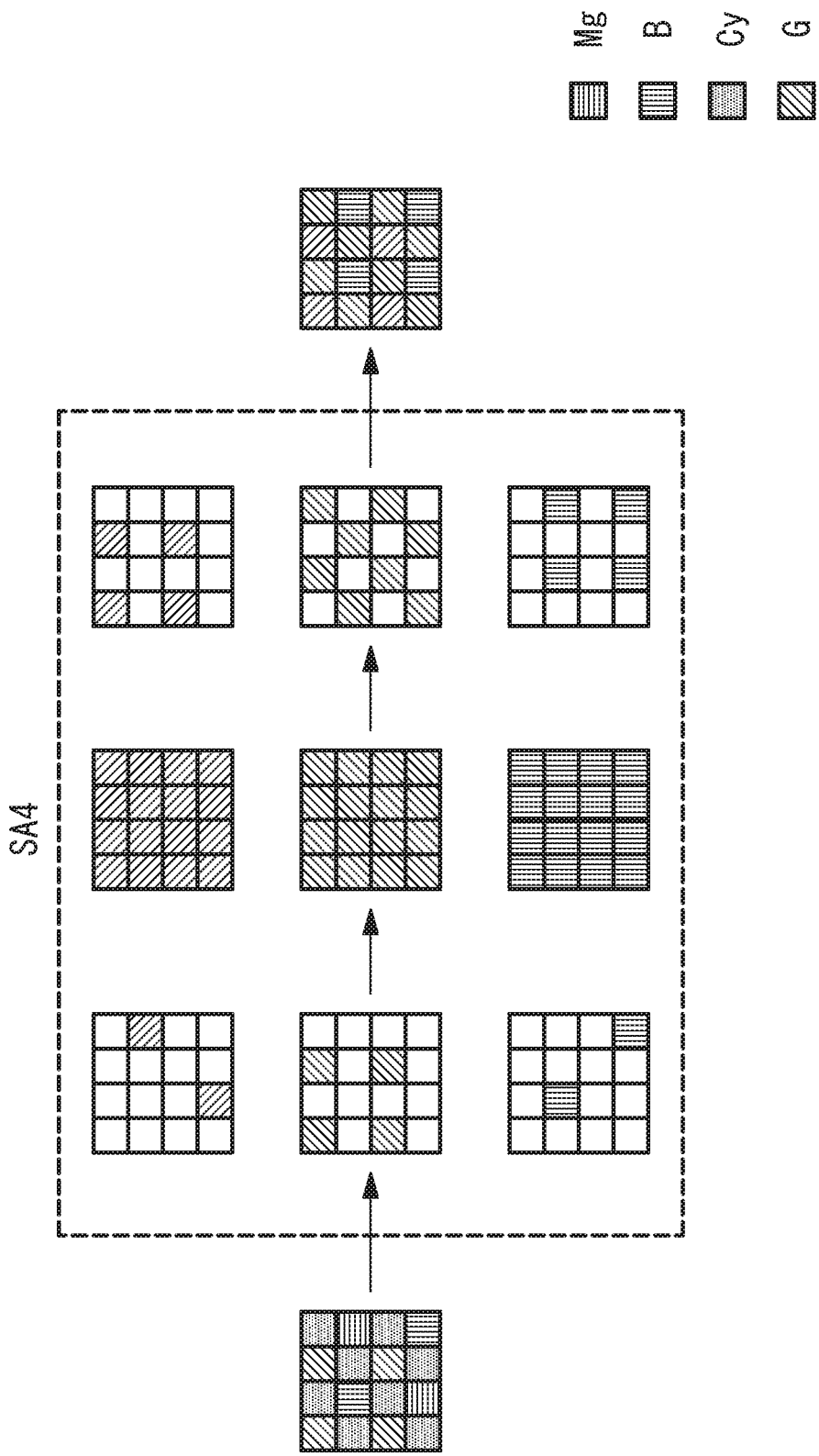
FIG. 18 is a diagram for explaining an example of Bayer-conversion processing, which is a third modification of the individual embodiments of the present invention.

In addition, as a third modification, as shown in FIG. 18, a frame-sequential image may be generated by generating RGB-information at positions of all pixels in the image data by means of demosaicing processing for the filter arrangement of the imaging device 31, and may subsequently be output being placed next to the Bayer array.

By doing so, in the case in which the demosaicing processing for the imaging device 31 is already available, it is possible to achieve the effects afforded by the individual embodiments, described above, without newly developing interpolation processing for performing conversion to the Bayer array from the imaging device 31.

Figure 19:
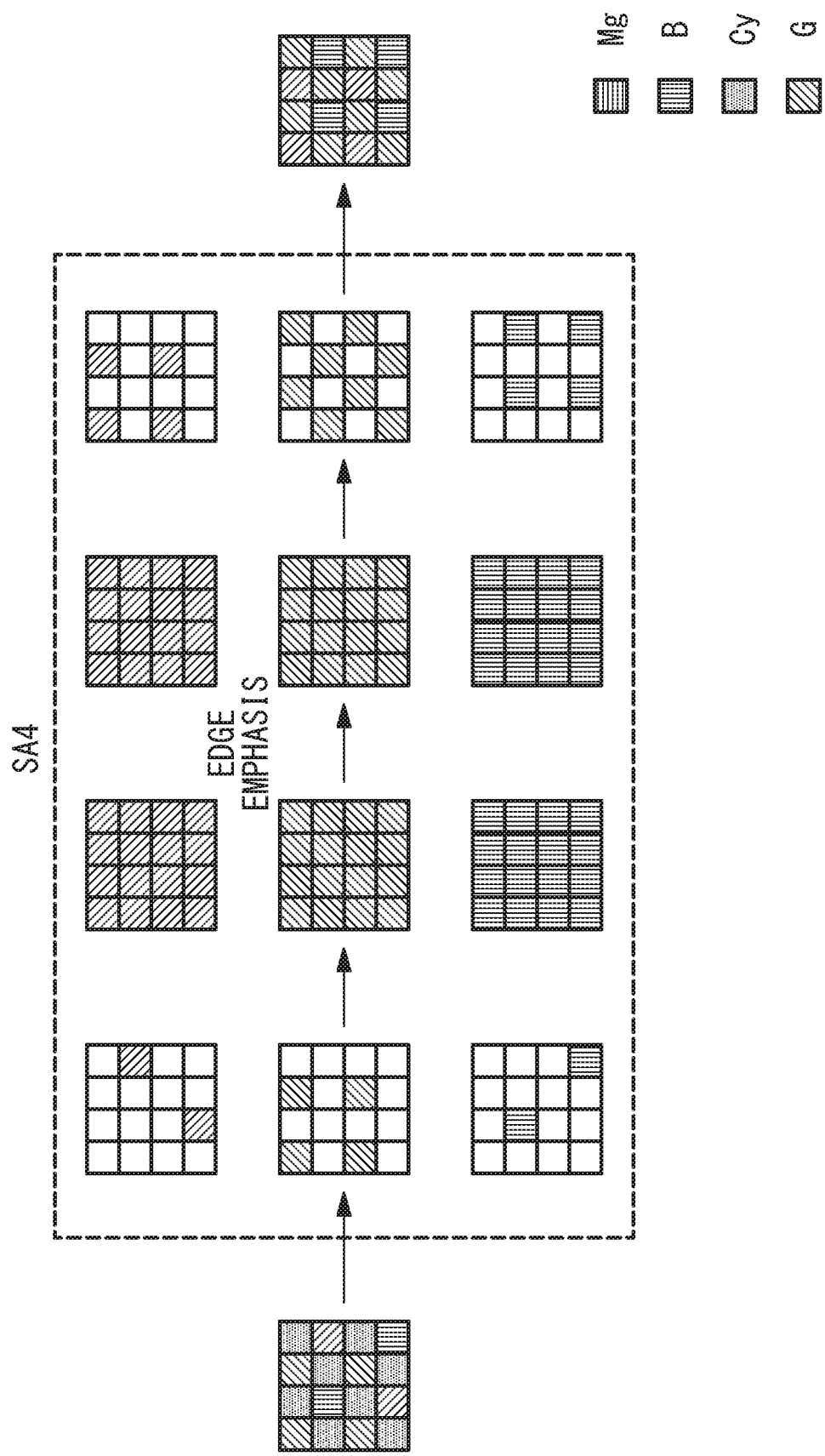
FIG. 19 is a diagram for explaining an example of Bayer-conversion processing, which is a fourth modification of the individual embodiments of the present invention.

In addition, as a fourth modification, as shown in FIG. 19, edge-emphasizing processing may be applied to the image data by means of the Bayer-conversion processing portion 39 and the image data may subsequently be converted to the Bayer array and output.

By being subjected to the edge-emphasizing processing once, the precision of direction discrimination is enhanced when performing demosaicing processing by means of the image-processing portion 63, and thus, it is possible to generate an observation image in which the sense of resolution is enhanced.

Figure 20:
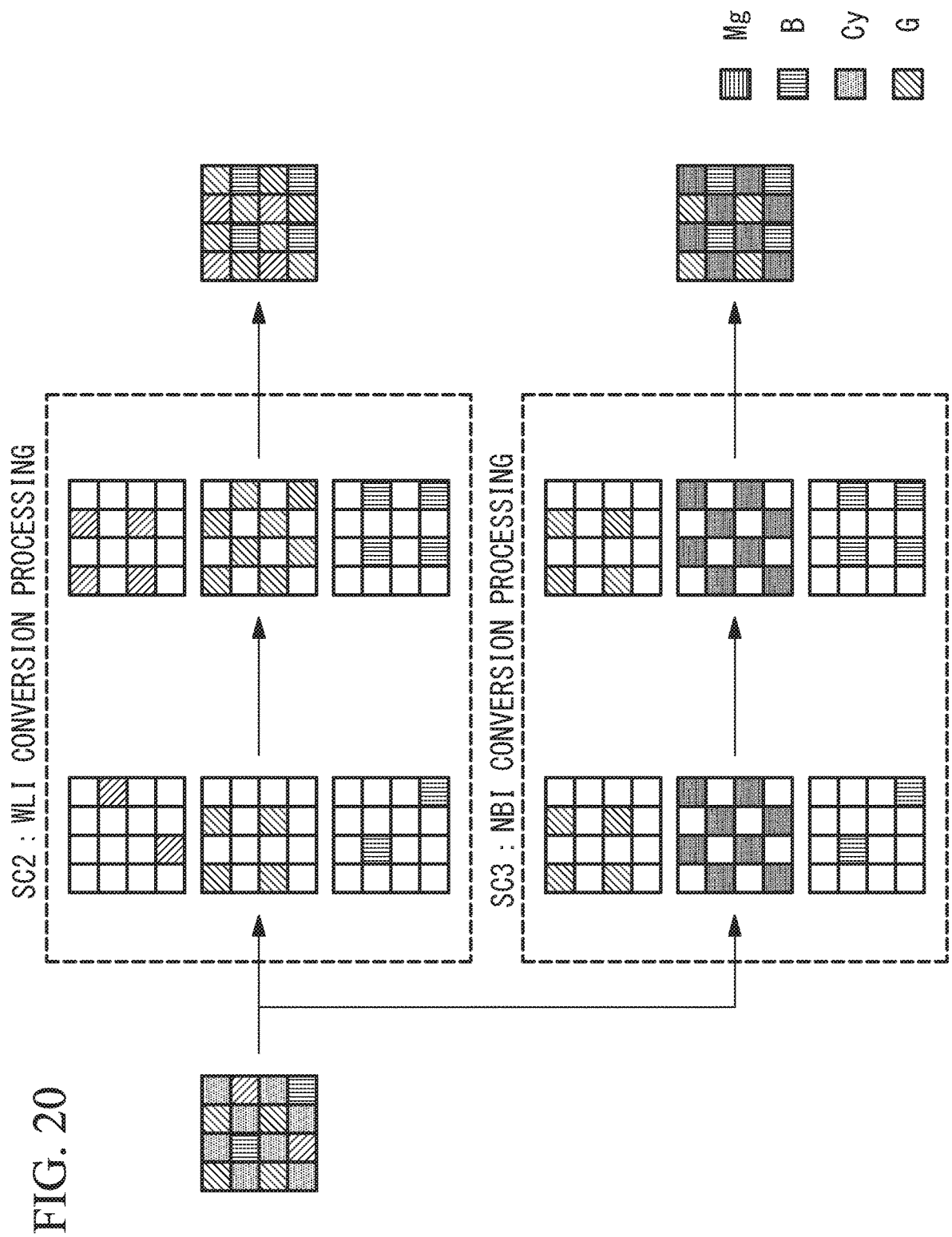
FIG. 20 is a diagram for explaining an example of Bayer-conversion processing, which is a fifth modification of the individual embodiments of the present invention.

Although the positions of pixels disposed in a checkered pattern are different between the case of the WLI conversion processing and the case of the NBI conversion processing in FIG. 11 showing a modification of the first embodiment, as a fifth modification, the Bayer conversion of the image data may be performed so that the positions of the pixels that are disposed in a checkered pattern after the Bayer conversion are the same between the case of the WLI conversion processing and the case of the NBI conversion processing, as shown in FIG. 20.

By doing so, because the positions of the pixels that are disposed in a checkered pattern are the same regardless of the light-source portion 3, it is possible to afford the same effects as those of the modifications of the individual embodiments, described above, without changing the parameters of the processor portion 5 for different light sources. In other words, it is possible to generate a highly precise observation image making full use of the performance of demosaicing processing for the Bayer array.

As above, although the embodiments of the present invention have been described in detail with reference to the drawings, specific configurations are not limited to those in the embodiments, and design alterations or the like within a range that does not depart from the scope of the present invention are also encompassed. For example, the present invention is not limited to each of the embodiments and modifications described above and may be applied to embodiments in which these embodiments and modifications are appropriately combined, and is not particularly limited.

As a result, the above-described embodiments lead to the following aspects.

A first aspect of the present invention is an endoscope scope including: an imaging device that acquires image information about an imaging subject; a color filter that is disposed on pixels of the imaging device and in which primary-color pixels and complementary-color pixels coexist; a compatibility-detecting portion that detects whether or not an image-processing apparatus that generates an observation image on the basis of the image information acquired by the imaging device via the color filter is compatible with the image information consisting of an array in which the primary-color pixels and the complementary-color pixels coexist; and a conversion processing portion that performs Bayer-conversion processing for converting the image information to be transmitted to the image-processing apparatus from the imaging device to a Bayer array in the case in which the compatibility-detecting portion detects that the image-processing apparatus is not compatible with the image information consisting of the array in which the primary-color pixels and the complementary-color pixels coexist, and that does not perform the Bayer-conversion processing on the image information to be transmitted to the image-processing apparatus from the imaging device in the case in which the compatibility-detecting portion detects that the image-processing apparatus is compatible with the image information consisting of the array in which the primary-color pixels and the complementary-color pixels coexist.

With this aspect, the imaging device is connected to the image-processing apparatus and inserted into a body cavity, and the image information for generating the observation image of the imaging subject by means of the image-processing apparatus is acquired by the imaging device via the color filter. In this case, the compatibility-detecting portion detects whether or not the image-processing apparatus is compatible with the image information consisting of the array in which the primary-color pixels and the complementary-color pixels coexist.

Also, the conversion processing portion applies the Bayer-conversion processing to the image information from the imaging device and transmits the image information to the image-processing apparatus in the case in which the compatibility-detecting portion detects that the image-processing apparatus is not compatible with the image information consisting of the array in which the primary-color pixels and the complementary-color pixels coexist, and the conversion processing portion transmits the image information from the imaging device to the image-processing apparatus without applying the Bayer-conversion processing thereto in the case in which the compatibility-detecting portion detects that the image-processing apparatus is compatible with the image information consisting of the array in which the primary-color pixels and the complementary-color pixels coexist.

Therefore, even in the case in which the image-processing apparatus is for Bayer processing, it is possible to precisely generate an observation image by means of the Bayer-processing image-processing apparatus regardless of the filter array of the imaging device without having to improve the Bayer-processing image-processing apparatus.

In the above-described aspect, the complementary-color pixels may be Cy-pixels.

By employing such a configuration, it is possible to acquire a greater amount of information about the blue wavelength band as compared with the case in which the color filter has only the primary-color pixels, and it is possible to achieve an effect of enhancing the resolution for capillaries or the like in the case of narrow-band light observation.

In the above-described aspect, the color filter may consist of the complementary-color pixels disposed in a checkered pattern.

By employing such a configuration, in the image-processing apparatus, it is possible to generate a highly precise observation image making full use of the performance of demosaicing processing for the Bayer array.

The above-described aspect may be provided with a light-source-type-detecting portion that detects whether or not the illumination light radiated onto the imaging subject is one of a white light and a predetermined narrow band light contained in the white light, wherein the conversion processing portion may convert the image information so that the G-pixels are in a checkered pattern in the case in which the compatibility-detecting portion detects that the image-processing apparatus is not compatible with the image information consisting of the array in which the primary-color pixels and the complementary-color pixels coexist and in the case in which the light-source-type-detecting portion detects that the illumination light is the white light, and the conversion processing portion may convert the image information so that the Cy-pixels are in a checkered pattern in the case in which the compatibility-detecting portion detects that the image-processing apparatus is not compatible with the image information consisting of the array in which the primary-color pixels and the complementary-color pixels coexist and in the case in which the light-source-type-detecting portion detects that the illumination light is the narrow band light.

As a result of the conversion processing portion converting the image information so that the G-pixels, which are highly correlated with the B-pixels as well as the R-pixels, are in a checkered pattern in the case in which the illumination light is the white-light, and converting the image information so that the Cy-pixels, which are highly correlated with the B-pixels as well as the G-pixels, are in a checkered pattern in the case in which the illumination light is the narrow-band light, in the image-processing apparatus, it is possible to generate a highly precise observation image making fuller use of the performance of demosaicing processing for the Bayer array.

In the above-described aspect, the conversion processing portion may convert the image information so that the positions of the pixels to be disposed in a checkered pattern after the Bayer-conversion processing are matched between the case in which the illumination light is the white-light and the case in which the illumination light is the narrow-band light.

By employing such a configuration, as a result of aligning the positions of the pixels to be disposed in a checkered pattern regardless of the type of the illumination light, it is possible to generate a highly precise observation image making full use of the performance of demosaicing processing for the Bayer array without changing the parameters of the image-processing apparatus for different types of the illumination light.

In the above-described aspect, the conversion processing portion may perform color conversion on the complementary-color pixels of the image information, thus performing a conversion to a Bayer array consisting only of primary-color pixels, in the case in which the compatibility-detecting portion detects that the image-processing apparatus is not compatible with the image information consisting of the array in which the primary-color pixels and the complementary-color pixels coexist.

By employing such a configuration, even in the case in which the complementary-color pixels are contained, it is possible to generate a highly precise observation image making full use of the performance of demosaicing processing for the Bayer array without altering a processing circuit of the image-processing apparatus.

In the above-described aspect, the conversion processing portion may apply the Bayer-conversion processing to the image information after applying edge-emphasizing processing thereto.

By employing such a configuration, the precision of the direction discrimination is enhanced in the case in which the image-processing apparatus performs demosaicing processing, and thus, it is possible to generate an observation image in which a sense of resolution is enhanced.

A second aspect of the present invention is an endoscope processor including: an Bayer-processing image-processing portion that generates an observation image on the basis of image information acquired by an imaging device of an endoscope scope; an array-detecting portion that detects whether or not the image information output from the imaging device of the connected endoscope scope consists of a Bayer array; and a conversion processing portion that applies Bayer-conversion processing for converting the image information transmitted to the image-processing portion from the imaging device to the Bayer array in the case in which the array-detecting portion does not detect that the image information consists of the Bayer array, and that does not apply the Bayer-conversion processing to the image information transmitted to the image-processing portion from the imaging device in the case in which the array-detecting portion detects that the image information consists of the Bayer array.

With this aspect, when the endoscope scope is connected, the endoscope scope is inserted into the body cavity, and the image information about the imaging subject is acquired by the imaging device, the image-processing portion processes that image information, thus generating an observation image. In this case, the array-detecting portion detects whether or not the image information output from the imaging device of the connected endoscope scope consists of the Bayer array.

Also, the conversion processing portion applies the Bayer-conversion processing to the image information from the imaging device and transmits the image information to the image-processing portion in the case in which the array-detecting portion does not detect that the image information consists of the Bayer array, and the conversion processing portion transmits the image information from the imaging device to the image-processing portion without applying the Bayer-conversion processing thereto in the case in which the array-detecting portion detects that the image information consists of the Bayer array.

Therefore, with the Bayer-processing image-processing portion, it is possible to precisely generate an observation image by means of the Bayer-processing image-processing portion regardless of the filter array of the imaging device without having to improve the Bayer-processing image-processing portion.

The above-described aspect may be provided with a light-source-type-detecting portion that detects whether or not illumination light radiated onto an imaging subject is one of a white light and a predetermined narrow band light contained in the white light, wherein the conversion processing portion may convert the image information so that G-pixels are in a checkered pattern in the case in which the array-detecting portion does not detect that the image information consists of the Bayer array and in the case in which the light-source-type-detecting portion detects that the illumination light is the white light, and the conversion processing portion may convert the image information so that Cy-pixels are in a checkered pattern in the case in which the array-detecting portion does not detect that the image information consists of the Bayer array and in the case in which the light-source-type-detecting portion detects that the illumination light is the narrow band light.

As a result of the conversion processing portion converting the image information so that the G-pixels, which are highly correlated with the B-pixels as well as the R-pixels, are in a checkered pattern in the case in which the illumination light is the white-light, and converting the image information so that the Cy-pixels, which are highly correlated with the B-pixels as well as the G-pixels, are in a checkered pattern in the case in which the illumination light is the narrow-band light, in the image-processing apparatus, it is possible to generate a highly precise observation image making fuller use of the performance of demosaicing processing for the Bayer array.

In the above-described aspect, the conversion processing portion may convert the image information so that the positions of the pixels to be disposed in a checkered pattern after the Bayer-conversion processing are matched between the case in which the illumination light is the white-light and the case in which the illumination light is the narrow-band light.

By employing such a configuration, as a result of aligning the positions of the pixels to be disposed in a checkered pattern regardless of the type of the illumination light, it is possible to generate a highly precise observation image making full use of the performance of demosaicing processing for the Bayer array without changing the parameters of the image-processing apparatus for different types of the illumination light.

In the above-described aspect, the conversion processing portion may perform color conversion on the complementary-color pixels of the image information, thus performing a conversion to a Bayer array consisting only of primary-color pixels, in the case in which the array-detecting portion does not detect that the image information consists of the Bayer array.

By employing such a configuration, even in the case in which the complementary-color pixels are contained, it is possible to generate a highly precise observation image making full use of the performance of demosaicing processing for the Bayer array without altering a processing circuit of the image-processing apparatus.

In the above-described aspect, the conversion processing portion may apply the Bayer-conversion processing to the image information after applying edge-emphasizing processing thereto.

By employing such a configuration, the precision of the direction discrimination is enhanced in the case in which the image-processing apparatus performs demosaicing processing, and thus, it is possible to generate an observation image in which the sense of resolution is enhanced.

A third aspect of the present invention is an endoscope adaptor that connects an endoscope scope that is provided with an imaging device, which acquires image information about an imaging subject, and that is inserted into a body cavity and a Bayer-processing image-processing apparatus, which generates an observation image based on the image information acquired by the imaging device, the endoscope adaptor including: an array-detecting portion that detects whether or not the image information output from the imaging device of the endoscope scope to be connected to the image-processing apparatus consists of the Bayer array; and a conversion processing portion that applies Bayer-conversion processing for converting the image information transmitted to the image-processing apparatus from the imaging device to the Bayer array in the case in which the array-detecting portion does not detect that the image information consists of the Bayer array, and that does not apply the Bayer-conversion processing to the image information transmitted to the image-processing apparatus from the imaging device in the case in which the array-detecting portion detects that the image information consists of the Bayer array.

With this aspect, when the endoscope scope and the image-processing apparatus are connected, the endoscope scope is inserted into the body cavity, and the imaging device acquires image information about an imaging subject, the image-processing apparatus processes that image information, thus generating an observation image. In this case, the compatibility-detecting portion detects whether or not the image information output from the imaging device of the endoscope scope consists of the Bayer array.

Also, the conversion processing portion applies the Bayer-conversion processing to the image information from the imaging device and transmits the image information to the image-processing apparatus in the case in which the array-detecting portion does not detect that the image information consists of the Bayer array, and the conversion processing portion transmits the image information from the imaging device to the image-processing apparatus without applying the Bayer-conversion processing thereto in the case in which the array-detecting portion detects that the image information consists of the Bayer array.

Therefore, with the Bayer-processing image-processing apparatus, it is possible to precisely generate an observation image by means of the Bayer-processing image-processing apparatus regardless of the filter array of the imaging device without having to improve the Bayer-processing image-processing apparatus.

The above-described aspect is provided with a light-source-type-detecting portion that detects whether or not illumination light radiated onto the imaging subject is one of a white light and a predetermined narrow band light contained in the white light, wherein the conversion processing portion may convert the image information so that G-pixels are in a checkered pattern in the case in which the array-detecting portion does not detect that the image information consists of the Bayer array and in the case in which the light-source-type-detecting portion detects that the illumination light is the white light, and the conversion processing portion may convert the image information so that Cy-pixels are in a checkered pattern in the case in which the array-detecting portion does not detect that the image information consists of the Bayer array and in the case in which the light-source-type-detecting portion detects that the illumination light is the narrow band light.

As a result of the conversion processing portion converting the image information so that the G-pixels, which are highly correlated with the B-pixels as well as the R-pixels, are in a checkered pattern in the case in which the illumination light is the white-light, and converting the image information so that the Cy-pixels, which are highly correlated with the B-pixels as well as the G-pixels, are in a checkered pattern in the case in which the illumination light is the narrow-band light, in the image-processing apparatus, it is possible to generate a highly precise observation image making fuller use of the performance of demosaicing processing for the Bayer array.

In the above-described aspect, the conversion processing portion may convert the image information so that the positions of the pixels to be disposed in a checkered pattern after the Bayer-conversion processing are matched between the case in which the illumination light is the white-light and the case in which the illumination light is the narrow-band light.

By employing such a configuration, as a result of aligning the positions of the pixels to be disposed in a checkered pattern regardless of the type of the illumination light, it is possible to generate a highly precise observation image making full use of the performance of demosaicing processing for the Bayer array without changing the parameters of the image-processing apparatus for different types of the illumination light.

In the above-described aspect, the conversion processing portion may perform color conversion on the complementary-color pixels of the image information, thus performing a conversion to a Bayer array consisting only of primary-color pixels, in the case in which the array-detecting portion does not detect that the image information consists of the Bayer array.

By employing such a configuration, even in the case in which the complementary-color pixels are contained, it is possible to generate a highly precise observation image making full use of the performance of demosaicing processing for the Bayer array without altering a processing circuit of the image-processing apparatus.

In the above-described aspect, the conversion processing portion may apply the Bayer-conversion processing to the image information after applying edge-emphasizing processing thereto.

By employing such a configuration, the precision of the direction discrimination is enhanced in the case in which the image-processing apparatus performs demosaicing processing, and thus, it is possible to generate an observation image in which the feeling of resolution is enhanced.

The present invention affords an advantage in that it is possible to precisely generate an image by means of a Bayer-processing image-processing apparatus regardless of a filter array of an imaging device without having to improve the Bayer-processing image-processing apparatus.

REFERENCE SIGNS LIST

1, 83 endoscope (endoscope scope)
31 imaging device
31*a* color filter
35 compatibility-detection processing portion (compatibility-detecting portion)
39, 71 Bayer-conversion processing portion (conversion processing portion)

63 image-processing portion (image-processing apparatus)
73 light-source-type-detection processing portion (light-source-type-detecting portion)
85, 93 compatibility-detection processing portion (array-detecting portion)
81 processor portion (endoscope processor)
91 endoscope adaptor

The invention claimed is:

1. An endoscope scope comprising:
an imaging device that acquires image information about an imaging subject;
a color filter that is disposed on pixels of the imaging device and in which primary-color pixels and complementary-color pixels coexist; and
a processor configured to:
detect whether or not an image processor that generates an observation image based on the image information acquired by the imaging device via the color filter is compatible with the image information consisting of an array in which the primary-color pixels and the complementary-color pixels coexist;
perform Bayer-conversion processing for converting the image information to be transmitted to the image processor from the imaging device to a Bayer array in a case in which it is detected that the image processor is not compatible with the image information consisting of the array in which the primary-color pixels and the complementary-color pixels coexist; and
not perform the Bayer-conversion processing on the image information to be transmitted to the image processor from the imaging device in a case in which it is detected that the image processor is compatible with the image information consisting of the array in which the primary-color pixels and the complementary-color pixels coexist.

2. The endoscope scope according to claim 1, wherein the complementary-color pixels are Cy-pixels.

3. The endoscope scope according to claim 2, wherein the color filter consists of the complementary-color pixels disposed in a checkered pattern.

4. The endoscope scope according to claim 2, wherein the processor is further configured to:
detect whether or not illumination light radiated onto the imaging subject is one of a white light and a predetermined narrow band light contained in the white light;
convert the image information so that G-pixels are in a checkered pattern in a case in which it is detected that (i) the image processor is not compatible with the image information consisting of the array in which the primary-color pixels and the complementary-color pixels coexist and (ii) the illumination light is the white light; and
convert the image information so that the Cy-pixels are in a checkered pattern in a case in which it is detected that (i) the image processor is not compatible with the image information consisting of the array in which the primary-color pixels and the complementary-color pixels coexist and (ii) the illumination light is the narrow band light.

5. The endoscope scope according to claim 4, wherein the processor is configured to convert the image information so that positions of the pixels to be disposed in a checkered pattern after the Bayer-conversion processing are matched between the case in which the illumination light is the white-light and the case in which the illumination light is the narrow-band light.

6. The endoscope scope according to claim 1, wherein the processor is configured to perform color conversion on the complementary-color pixels of the image information, thus performing a conversion to a Bayer array consisting only of primary-color pixels, in the case in which it is detected that the image processor is not compatible with the image information consisting of the array in which the primary-color pixels and the complementary-color pixels coexist.

7. The endoscope scope according to claim 1, wherein the processor is configured to apply the Bayer-conversion processing to the image information after applying edge-emphasizing processing thereto.

8. An endoscope processor comprising:
an image processor that generates an observation image based on image information acquired by an imaging device of an endoscope scope;
a first detector that detects whether or not the image information output from the imaging device of the connected endoscope scope consists of a Bayer array; and
a converter that applies Bayer-conversion processing for converting the image information transmitted to the image processor from the imaging device to the Bayer array in a case in which the first detector does not detect that the image information consists of the Bayer array, and that does not apply the Bayer-conversion processing to the image information transmitted to the image processor from the imaging device in a case in which the first detector detects that the image information consists of the Bayer array.

9. The endoscope processor according to claim 8, further comprising:
a second detector that detects whether or not illumination light radiated onto an imaging subject is one of a white light and a predetermined narrow band light contained in the white light,
wherein the converter converts the image information so that G-pixels are in a checkered pattern in the case in which the first detector does not detect that the image information consists of the Bayer array and in a case in which the second detector detects that the illumination light is the white light, and the converter converts the image information so that Cy-pixels are in a checkered pattern in the case in which the first detector does not detect that the image information consists of the Bayer array and in a case in which the second detector detects that the illumination light is the narrow band light.

10. The endoscope processor according to claim 9, wherein the converter converts the image information so that positions of the pixels to be disposed in a checkered pattern after the Bayer-conversion processing are matched between the case in which the illumination light is the white-light and the case in which the illumination light is the narrow-band light.

11. The endoscope processor according to claim 8, wherein the converter performs color conversion on complementary-color pixels of the image information, thus performing a conversion to a Bayer array consisting only of primary-color pixels, in the case in which the first detector does not detect that the image information consists of the Bayer array.

12. The endoscope processor according to claim 8, wherein the converter applies the Bayer-conversion processing to the image information after applying edge-emphasizing processing thereto.

13. An endoscope adaptor that connects (i) an endoscope scope that is provided with an imaging device which acquires image information about an imaging subject, the endoscope scope being insertable into a body, and (ii) an image processor which generates an observation image based on the image information acquired by the imaging device, the endoscope adaptor comprising a processor configured to:

detect whether or not the image information output from the imaging device of the endoscope scope to be connected to the image processor consists of a Bayer array;

apply Bayer-conversion processing for converting the image information transmitted to the image processor from the imaging device to the Bayer array in a case in which it is detected that the image information does not consist of the Bayer array; and not apply the Bayer-conversion processing to the image information transmitted to the image processor from the imaging device in a case in which it is detected that the image information consists of the Bayer array.

14. The endoscope adaptor according to claim 13, wherein the processor is further configured to:

detect whether or not illumination light radiated onto the imaging subject is one of a white light and a predetermined narrow band light contained in the white light;

convert the image information so that G-pixels are in a checkered pattern in a case in which it is detected that (i) the image information does not consist of the Bayer array and (ii) the illumination light is the white light; and convert the image information so that Cy-pixels are in a checkered pattern in a case in which it is detected that (i) the image information does not consist of the Bayer array and (ii) the illumination light is the narrow band light.

15. The endoscope adaptor according to claim 14, wherein the processor is configured to convert the image information so that positions of the pixels to be disposed in a checkered pattern after the Bayer-conversion processing are matched between the case in which the illumination light is the white-light and the case in which the illumination light is the narrow-band light.

16. The endoscope adaptor according to claim 13, wherein the processor is configured to perform color conversion on complementary-color pixels of the image information, thus performing a conversion to a Bayer array consisting only of primary-color pixels, in the case in which it is detected that the image information does not consist of the Bayer array.

17. The endoscope adaptor according to claim 13, wherein the processor is configured to perform the Bayer-conversion processing to the image information after applying edge-emphasizing processing thereto.

* * * * *